(12) United States Patent
Laderman et al.

(10) Patent No.: US 10,788,498 B2
(45) Date of Patent: *Sep. 29, 2020

(54) IBS SENSITIVITY TESTING

(71) Applicant: Biomerica, Inc., Irvine, CA (US)

(72) Inventors: Elisabeth Laderman, Irvine, CA (US); Zackary Irani-Cohen, Irvine, CA (US)

(73) Assignee: Biomerica, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/385,322

(22) Filed: Apr. 16, 2019

(65) Prior Publication Data

US 2019/0242901 A1    Aug. 8, 2019

Related U.S. Application Data

(62) Division of application No. 15/526,240, filed as application No. PCT/US2015/060759 on Nov. 13, 2015.

(60) Provisional application No. 62/079,783, filed on Nov. 14, 2014.

(51) Int. Cl.
  *G01N 33/68* (2006.01)
  *G01N 33/543* (2006.01)

(52) U.S. Cl.
  CPC ....... *G01N 33/6845* (2013.01); *G01N 33/543* (2013.01); *G01N 2800/065* (2013.01)

(58) Field of Classification Search
  None
  See application file for complete search history.

(56) References Cited

U.S. PATENT DOCUMENTS

| | | | |
|---|---|---|---|
| 4,208,479 A | 6/1980 | Zuk et al. | |
| 6,152,887 A | 11/2000 | Blume | |
| 6,458,550 B1 | 10/2002 | Luborsky | |
| 7,601,509 B2 | 10/2009 | Power | |
| 7,756,604 B1 | 7/2010 | Davis et al. | |
| 10,309,970 B2 | 6/2019 | Laderman et al. | |
| 2002/0002270 A1 | 1/2002 | Zinkowski et al. | |
| 2003/0143627 A1 | 7/2003 | Vojdani | |
| 2004/0072272 A1 | 4/2004 | Fine | |
| 2004/0091843 A1 | 5/2004 | Albro et al. | |
| 2005/0181163 A1 | 8/2005 | Kose | |
| 2005/0187656 A1 | 8/2005 | Walker et al. | |
| 2005/0255533 A1 | 11/2005 | Dantini et al. | |
| 2006/0275846 A1 | 12/2006 | Dorval et al. | |
| 2007/0117217 A1 | 5/2007 | Lal et al. | |
| 2007/0122840 A1 | 5/2007 | Cousins | |
| 2007/0298447 A1 | 12/2007 | Fine | |
| 2008/0073430 A1 | 3/2008 | Sickenius | |
| 2009/0208984 A1 | 8/2009 | Scott et al. | |
| 2009/0253154 A1 | 10/2009 | Vojdani | |
| 2010/0190191 A1 | 7/2010 | Dodds | |
| 2010/0227340 A1 | 9/2010 | Rozenshteyn et al. | |
| 2011/0276344 A1 | 11/2011 | Williams | |
| 2011/0318717 A1 | 12/2011 | Adamowicz | |
| 2012/0005222 A1 | 1/2012 | Bhagwan et al. | |
| 2012/0058497 A1 | 3/2012 | Suga et al. | |
| 2013/0085345 A1 | 4/2013 | Geisner et al. | |
| 2013/0183692 A1 | 7/2013 | Dodds | |
| 2014/0322678 A1 | 10/2014 | Briancon et al. | |
| 2014/0324899 A1 | 10/2014 | Sherman et al. | |
| 2014/0348935 A1 | 11/2014 | Simon | |
| 2015/0036138 A1 | 2/2015 | Watson et al. | |
| 2016/0022746 A1* | 1/2016 | Lawley | C12Q 1/04 424/93.3 |
| 2016/0058377 A1 | 3/2016 | Butte et al. | |
| 2016/0145670 A1 | 5/2016 | Steger et al. | |
| 2018/0144821 A1 | 5/2018 | Irani-Cohen et al. | |
| 2018/0364252 A1 | 12/2018 | Irani-Cohen et al. | |
| 2019/0004039 A1 | 1/2019 | Irani-Cohen et al. | |
| 2019/0056408 A1 | 2/2019 | Irani-Cohen et al. | |
| 2019/0120835 A1 | 4/2019 | Irani-Cohen et al. | |
| 2019/0145972 A1 | 5/2019 | Irani-cohen et al. | |
| 2019/0170767 A1 | 6/2019 | Irani-cohen et al. | |
| 2019/0170768 A1 | 6/2019 | Irani-cohen et al. | |
| 2019/0242886 A1 | 8/2019 | Irani-cohen et al. | |
| 2019/0242904 A1 | 8/2019 | Irani-cohen et al. | |
| 2020/0003769 A1 | 1/2020 | Laderman et al. | |

FOREIGN PATENT DOCUMENTS

| | | |
|---|---|---|
| DE | 102013014080 A1 | 3/2015 |
| EP | 1051626 A1 | 11/2000 |
| EP | 1548664 A1 | 6/2005 |
| JP | 2011178679 A | 9/2011 |
| KR | 20090108968 A | 10/2009 |
| KR | 20130127145 A | 11/2013 |
| WO | WO-2002029415 A1 | 4/2002 |
| WO | WO-2004099785 A1 | 11/2004 |
| WO | WO-2008121406 A1 | 10/2008 |
| WO | WO-2009035529 A1 | 3/2009 |
| WO | WO-2010/049726 A1 | 5/2010 |

OTHER PUBLICATIONS

Nonlinear Dynamics (Nonlinear Dynamics 2012; total 4 pages) (Year: 2012).*
Benjamini et al. (Behavioural Brain Research 2001 125: 279-284) (Year: 2001).*
Anbardan et al. (J. Neurogastroenterol Motil. 2012 18:70-77). (Year: 2012).*
ELISA Protocol (Thermo Scientific 2010) (Year: 2010).*
Camilleri et al. (Clin. Gastroenterol. Hepatol. 2008 6: 772-781) (Year: 2008).*
Payne (Gender Medicine 2004 1: 18-28) (Year: 2004).*
U.S. Appl. No. 15/759,088, US 2019-0056408 A1, Feb. 21, 2019 Irani-Cohen et al.

(Continued)

*Primary Examiner* — Changhwa J Cheu
(74) *Attorney, Agent, or Firm* — Womble Bond Dickinson (US) LLP; Danielle L. Herritt; Kevin A. Fiala

(57) ABSTRACT

Contemplated test kits and methods for food sensitivity are based on rational-based selection of food preparations with established discriminatory p-value. Particularly preferred kits include those with a minimum number of food preparations that have an average discriminatory p-value of ≤0.07 as determined by their raw p-value or an average discriminatory p-value of ≤0.10 as determined by FDR multiplicity adjusted p-value. In further contemplated aspects, compositions and methods for food sensitivity are also stratified by gender to further enhance predictive value.

25 Claims, 15 Drawing Sheets

(56) References Cited

OTHER PUBLICATIONS

U.S. Appl. No. 15/875,990, US 2018-0144821 A1, May 24, 2018 Irani-Cohen et al.
U.S. Appl. No. 16/013,774, US 2018-0364252 A1, Dec. 20, 2018 Irani-Cohen et al.
U.S. Appl. No. 16/013,821, US 2019-0004039 A1, Jan. 3, 2019 Irani-Cohen et al.
U.S. Appl. No. 16/131,281, US 2019-0145972 A1, May 16, 2019 Irani-Cohen et al.
U.S. Appl. No. 16/124,473, US 2019-0120835 A1, Apr. 25, 2019 Irani-Cohen et al.
U.S. Appl. No. 16/170,969, US 2019-0170767 A1, Jun. 6, 2019 Irani-Cohen et al.
U.S. Appl. No. 16/171,154, US 2019-0170768 A1, Jun. 6, 2019 Irani-Cohen et al.
U.S. Appl. No. 16/218,054, Not published.
U.S. Appl. No. 16/242,519, Not published.
U.S. Appl. No. 16/441,902, Not published.
U.S. Appl. No. 16/242,519.
U.S. Appl. No. 16/441,902.
U.S. Appl. No. 16/218,054.
Yu, K., "Ubiquitous Allergens, <Do you eat right?>." Sichuan Science and Technology Press, 126-129, (Mar. 2013).
Foster, A.P. et al., "Serum IgE and IgG responses to food antigens in normal and atopic dogs, and dogs with gastrointestinal disease", Veterinary Immunology and Immunopathology, 92(3-4), 113-124 (May 2003).
Traczyk, I. et al., "Concentration of IgG antibodies against food allergens in patients with irritable bowel syndrome and healthy individuals", Gastroenterology Review., 6(6), 382-387 (Dec. 2011).
Bohn, L. et al., Self-Reported Food-Related Gastrointestinal Symptoms in IBS Are Common and Associated With More Severe Symptoms and Reduced Quality of Life; Am J Gastroenterol., 108(5), 645-641 (May 2013).
Park, M-I. et al., Is there a role of food allergy in irritable bowel syndrome and functional dyspepsia? A systematic review, Neurogastroenterol Motil., 18, 595-607 (2006).
Cuomo, Rosario et al., Irritable bowel syndrome and food interaction, World Journal of Gastroenterology, 20(27), 8837-8845 (Jul. 21, 2014).
International Preliminary Report on Patentability for Application No. PCT/US2015/060759, dated Feb. 10, 2017, 7 pages.
International Search Report and Written Opinion for Application No. PCT/US2015/060759, dated Feb. 29, 2016, 16 pages.
Zuo, X.L. et al., Alterations of food antigen-specific serum immunoglobulins G and E antibodies in patients with irritable bowel syndrome and functional dyspepsia, Clinical and Experimental Allergy, 37, 823-830 (2007).
Atkinson, W. et al., "Food elimination based on IgG antibodies in irritable bowel syndrome: a randomised controlled trial", Dept. of Medicine, University Hospital of South Manchester, Manchester, UK, 53, 1459-1464 (Mar. 3, 2016).
Monsbakken, K.W. et al., Perceived food intolerance in subjects with irritable bowel syndrome—otology, prevalence and consequences; European Journal of Clinical Nutrition; 667-672 (2006).
Zeng, Qiang et al. "Variable Food-Specific IgG Antibody Levels in Healthy and Symptomatic Chinese Adults," PLOS One, Research Article, Jan. 3, 2013.
Alpay, et al. "Diet restriction in migraine, based on IgG against foods: a clinical double-blind, randomised, cross-over trial," Cephalalgia, 30:7, pp. 829-837, 2010.
Mitchell, et al. "Randomised controlled trial of food elimination diet based on IgG antibodies for the Prevention of migraine like headaches," Nutrition Journal 2011, 10:85.
Zhai, et al., "The Detection of Food-intolerance IgG Antibodies in Patient with Psoriasis," The Chinese Journal of Dermatoenereology, vol. 11 (2011).
Pizza, V. et al., "Food Intolerance in Migraine", Pharmacologyonline, 1:18-24 (2013).
Sun-Edelstein, Christina et al., "Foods and Supplements in the Management of Migraine Headaches", Clinical J. Pain, 25:446-452 (2009).
Gokani, T., Diet Restriction in Migraine, Based on IgG Against Foods: A Clinical Double-Blind, Randomised, Cross-Over Trial, Headache, 52:1056-1057 (2012).
Teixido, Michael et al., "Migraine-More than a Headache" (2014).
Constantinides, et al., "Migraine and tension-type headache triggers in a Greek population," Arquivos De Neuro-Psiquiatria, 73(8):665-669, (Aug. 2015).
Szabo, I. et al., "Allergenicity of major cow's mil and peanut proteins determined by IgE and IgG immunoblotting", Allergy, 55, 42-49, 2000.
Cai, Chenwen et al, "Serological investigation of food specific immunoglobulin G antibodies in patients with inflammatory bowel disease", PLoS One, 9(11), e112154 (1-8), (Nov. 13, 2014).
Nigg, Joel T. et al., Restriction and Elimination Diets in ADHD Treatment, Child Adolesc Psychiatr Clin N. Am., 23(4), 937-953 (Oct. 2014).
Kleter, Gijs A. et al., "Screening of transgenic proteins expressed in transgenic food crops for the presence of short amino acid sequences identical to potential, IgE-binding linear epitopes of allergens", BMC Structural Biology, 2(8), 1-11, (Dec. 12, 2002).
Carvalho, Roberta Villas Boas. et al., "Food Intolerance, Diet Composition, and Eating Patterns in Functional Dyspepsia Patients", Digestive Disease and Sciences, 55(1), 60-65 (2010).
Dias Batista, Emmanuelle et al., "Food intake assessment and quality of life in women with fibromyalgia", Revista Brasileira de Reumatologia, 56(2), 105-110 (Mar. 2016).
Sampson et al., "Relationship between food-specific IgE concentrations and the risk of positive food challenges in children and adolescents", J. Allergy Clin. Immunol., vol. 100(4): 444-451 (1997).
Sampson, HA, "Utility of food-specific IgE concentrations in predicting symptomatic food allergy", J. Allergy Clin, Immunol., vol. 107(5): 891-896 (2001).
Van Den Bogaerde, J. et al., "Gut mucosal response to food antigens in Crohn's disease", Alimentary Pharmacology & Therapeutics, vol. 16(11):1903-1915, (2002).
Takaaki, Kawaguchi et al., "Food antigen-induced immune responses in Crohn's disease patients and experimental colitis", Journal of Gastroenterology, vol. 50(4):394-405 (2014).
Correa, J.C., "Diagnosticos de Regresion Usando la FDR (Tasa de Descubrimientos Falsos)", Comunicaciones en Estadistica, vol. 3(2) (Dec. 2010).
Caselli, Michele et al., "A Possible Role of Food Intolerance in the Pathogenesis of Gastroesophageal Reflux Disease" The American Journal of Gastroenterology (Jan. 2009).
Caselli, Michele et al., "Test-based exclusion diets in gastroesophageal reflux disease patients: A randomized controlled pilot trial", The Word Journal of Gastroenterology, vol. 20(45): 17190-17195 (Jan. 2014).
Rodrigues Mariano De Almeida Rezende, Erica et al., "Clinical characteristics and sensitivity to food and inhalants among children with eosinophilic esophagitis", BMC Research Notes, BioMed Central Ltd., vol. 7(1): 1-7 (Jan. 2014).
Parker, Gordon et al., "Treatment-resistant depression: when antidepressant drug intolerance may indicate food intolerance", Australian and New Zealand Journal of Psychiatry, vol. 36(2): 263-265 (Apr. 2002).
Carr, Anitra C., "Depressed mood associated with gluten sensitivity—resolution of symptoms with a gluten free diet", The New Zealand Medical Journal, vol. 125(1366): 81-82 (Nov. 2012).
Dahiru, Tukur et al., "P-Value, a True Test of Statistical Significance? A Cautionary Note", Annals of Ibadan Postgraduate Medicine, vol. 6(1): 21-26 (2008).
Chinese Non-Patent Literature, Disease Enters Through the Mouth (2013), pp. 1-6.
Pelsser, Lidy M.J., "ADHD, a Food-Induced Hypersensitivity Syndrome: in Quest of a Cause," retrieved from the Internet: URL:https://

(56) References Cited

OTHER PUBLICATIONS www.adhdenvoeding.nl/wp-content/uploads/2016/10/1.Proefschrift-ADHD-en-Voeding (2011).

\* cited by examiner

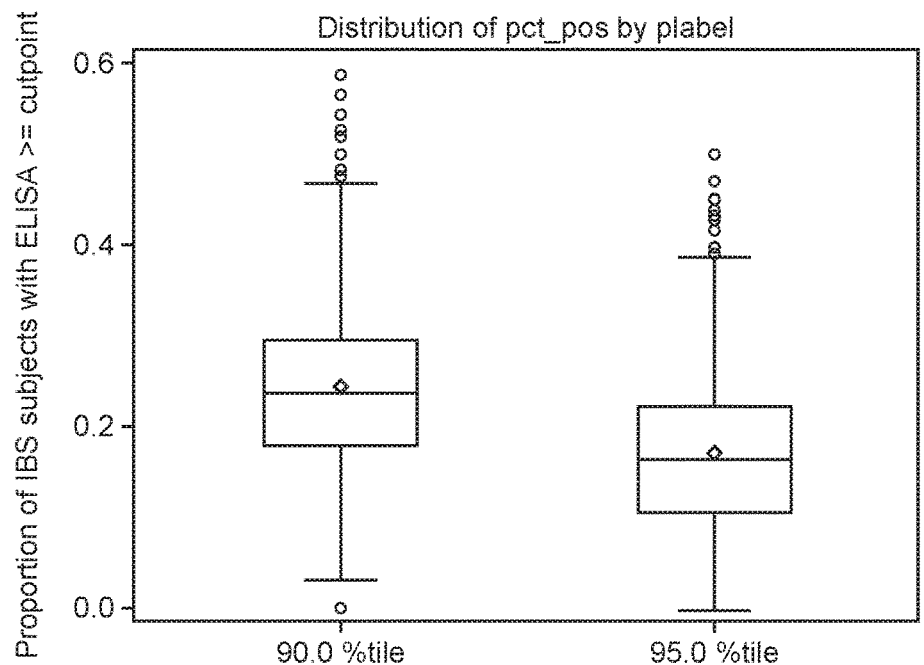
FIG. 1B
FIG. 1D
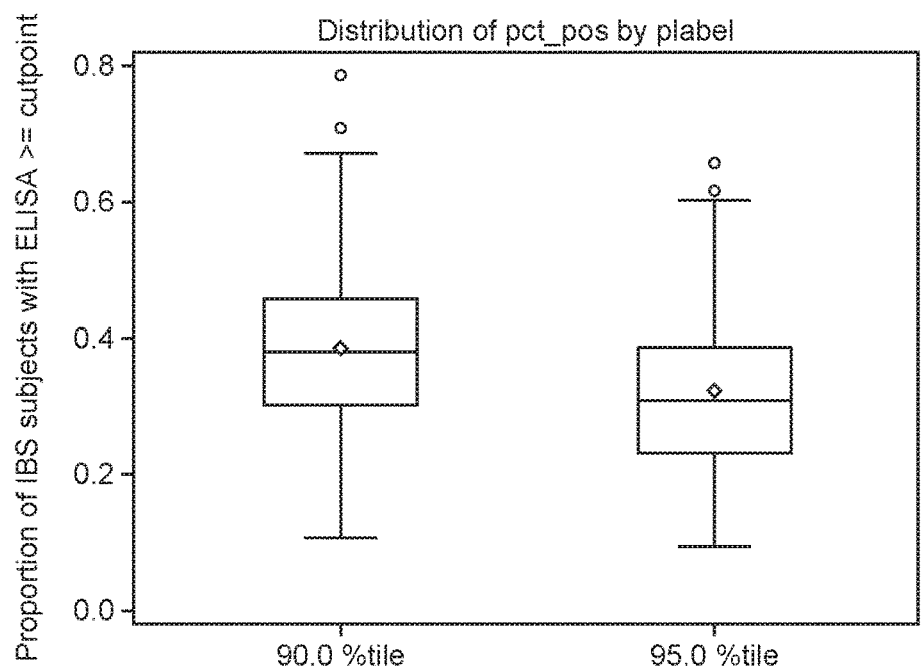

*Distribution of Percentage of IBS Subjects with Signals >= Control Cutpoint across 1000 Bootstrapped Samples*
Sex=M   Food=Rye
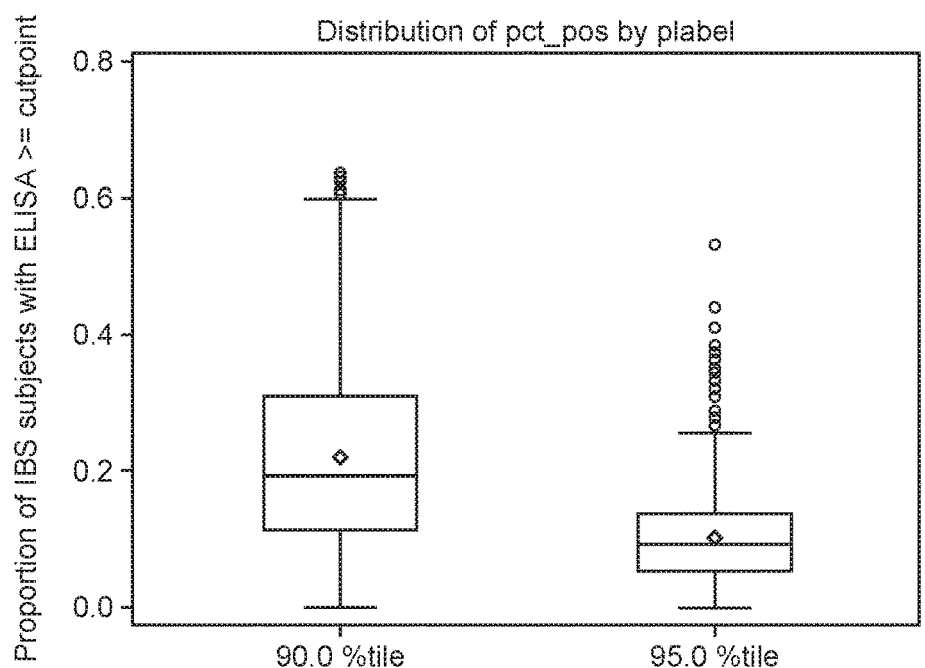
FIG. 3B
FIG. 3D
*Distribution of Percentage of IBS Subjects with Signals >= Control Cutpoint across 1000 Bootstrapped Samples*
Sex=F   Food=Rye
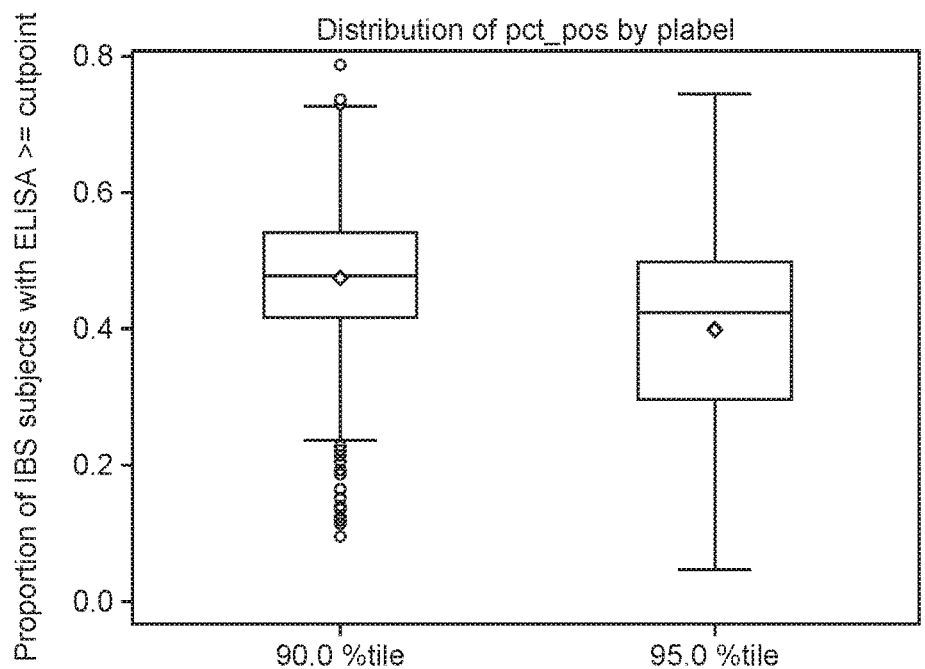

*Distribution of Percentage of IBS Subjects with Signals >= Control Cutpoint across 1000 Bootstrapped Samples*
Sex=M   Food=BlackTea

*Distribution of Percentage of IBS Subjects with Signals >= Control Cutpoint across 1000 Bootstrapped Samples*
Sex=F   Food=BlackTea

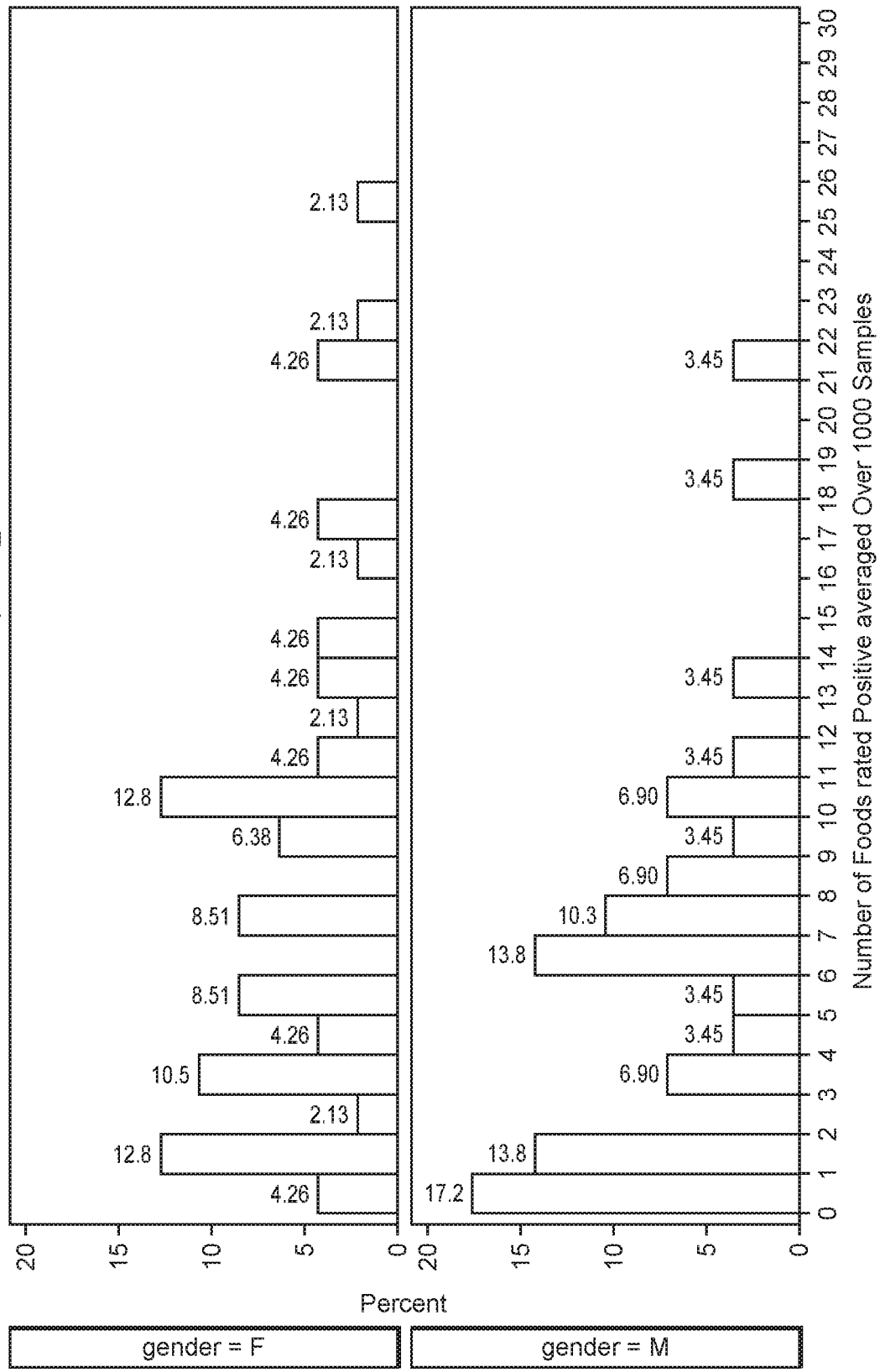

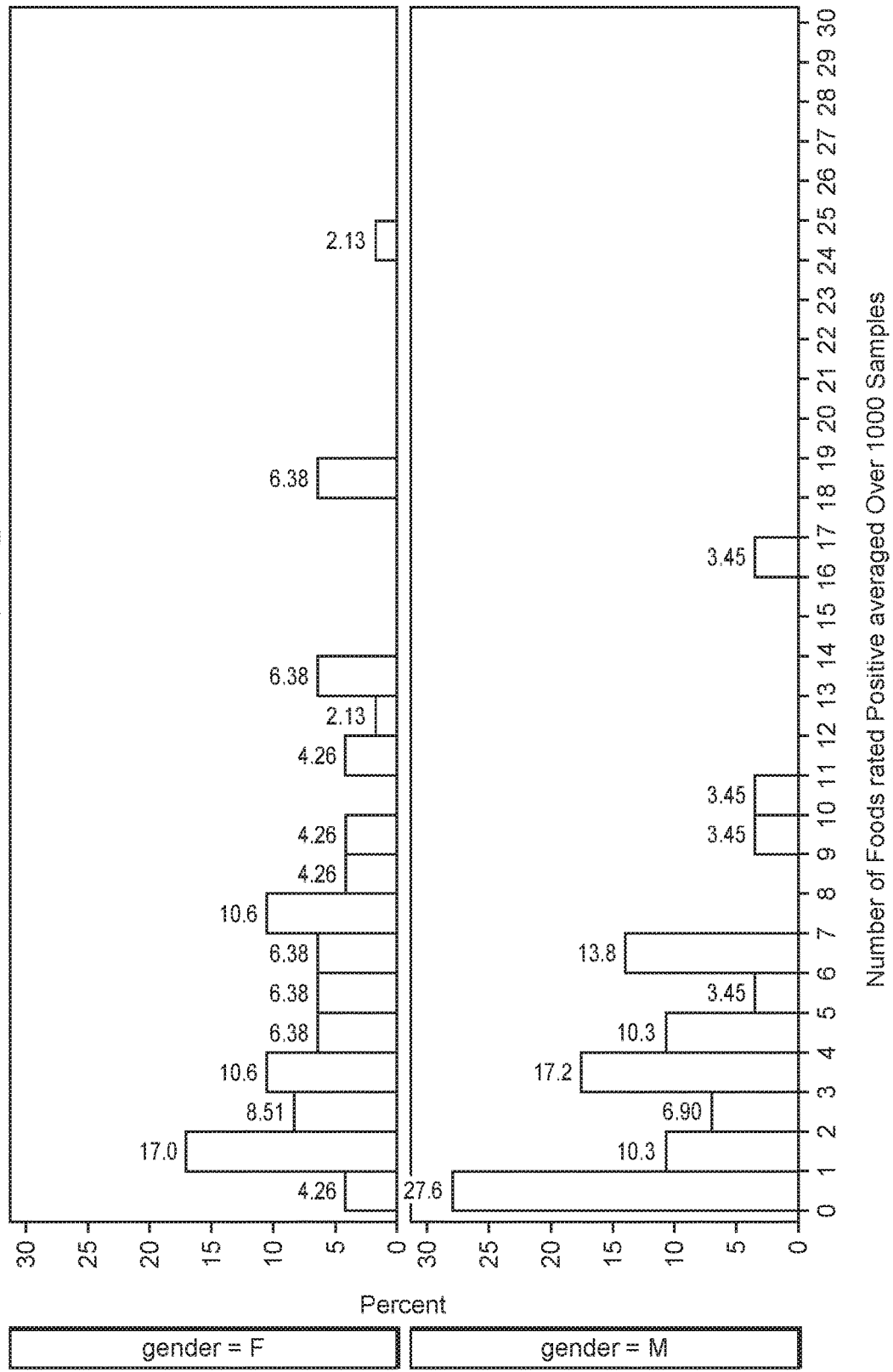

IBS SENSITIVITY TESTING

CROSS REFERENCE TO RELATED APPLICATIONS

This application is a divisional of U.S. patent application Ser. No. 15/526,240 filed May 11, 2017, now allowed, which is a 371 National Stage Application of PCT/US15/60759 filed Nov. 13, 2015 which claims the benefit of priority to our United States provisional patent application with Ser. No. 62/079,783 filed Nov. 14, 2014. The entire contents of the foregoing are incorporated herein by reference.

FIELD OF THE INVENTION

The field of the invention is sensitivity testing for food intolerance, and especially as it relates to testing and possible elimination of selected food items as trigger foods for patients diagnosed with or suspected to have irritable bowel syndrome.

BACKGROUND

The background description includes information that may be useful in understanding the present invention. It is not an admission that any of the information provided herein is prior art or relevant to the presently claimed invention, or that any publication specifically or implicitly referenced is prior art.

Food sensitivity, especially as it relates to irritable bowel syndrome (IBS), often presents with chronic abdominal pain, discomfort, bloating, and/or change in bowel habits and is not well understood in the medical community. Most typically, IBS is diagnosed by elimination of other pathological conditions (e.g., bacterial or protozoan infection, lactose intolerance, etc.) that may have similar or overlapping symptoms. However, IBS is often quite diverse with respect to dietary items triggering symptoms, and no standardized test to help identify trigger food items with a reasonable degree of certainty is known, leaving such patients often to trial-and-error.

While there are some commercially available tests and labs to help identify trigger foods, the quality of the test results from these labs is generally poor as is reported by a consumer advocacy group (e.g., http://www.which.co.uk/news/2008/08/food-allergy-tests-could-risk-your-health-154711/). Most notably, problems associated with these tests and labs were high false positive rates, high false negative rates, high intra-patient variability, and inter-laboratory variability, rendering such tests nearly useless. Similarly, further inconclusive and highly variable test results were also reported elsewhere (Alternative Medicine Review, Vol. 9, No. 2, 2004: pp 198-207), and the authors concluded that this may be due to food reactions and food sensitivities occurring via a number of different mechanisms. For example, not all IBS patients show positive response to food A, and not all IBS patients show negative response to food B. Thus, even if an IBS patient shows positive response to food A, removal of food A from the patient's diet may not relieve the patient's IBS symptoms. In other words, it is not well determined whether food samples used in the currently available tests are properly selected based on the high probabilities to correlate sensitivities to those food samples to IBS.

Many have made efforts to select food items or allergens to include in the test panel for immunoassay tests. For example, US Patent Application No. 2007/0122840 to Cousins discloses selection of 29 food allergens that are included in the test panel for ELISA assay. The 29 food allergens are selected based on the frequency of IgG positivity in preliminary experiments with a larger panel of food allergens. However, Cousins fails to teach any quantitative and/or statistical analysis for the selected antigens and as such fails to provide any rationale for the selection. Indeed, Cousin's method to select 29 food allergens for test panel has been criticized that the selection is rather arbitrary. For example, Croft criticized in a paper titled "IgG food antibodies and irritating the bowel", published in Gastroenterology, Vol. 128, Issue 4, p. 1135-1136, that Cousin's method is not clear whether the quantity and range of food antibodies being measured are similar or completely different to non-IBS patients or non-food intolerant patients because it lacks controls (normal or non-IBS control subject). Thus, it is at best unclear if Cousins achieves any improvement with respect to false positive and false negative results.

For another example, US Patent Application No. 2011/0306898 to Stierstorfer discloses selection of 41 food substances as test materials on skin patches. The 41 food substances are selected based on chemical compounds included in the food substances (e.g., vanillin, cinnamic aldehyde, sorbic acid, etc.). The food substances are tested on IBS patients or IBS-suspected patients for allergic contact dermatitis. However, Stierstorfer also fails to disclose how the false positive or false negative food allergens are eliminated and whether the food allergens are selected based on the gender stratification among IgG positivity results.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, even though various tests for food sensitivities are known in the art, all or almost all of them suffer from one or more disadvantages. Therefore, there is still a need for improved compositions, devices, and methods of food sensitivity testing, especially for identification and possible elimination of trigger foods for patients identified with or suspected of having IBS.

SUMMARY OF THE INVENTION

The inventive subject matter provides systems and methods for testing food intolerance in patients diagnosed with or suspected to have irritable bowel syndrome. One aspect of the invention is a test kit with for testing food intolerance in patients diagnosed with or suspected to have irritable bowel syndrome. The test kit includes a plurality of distinct food preparations coupled to individually addressable respective solid carriers. The plurality of distinct food preparations have an average discriminatory p-value of ≤0.07 as determined by raw p-value or an average discriminatory p-value of ≤0.10 as determined by FDR multiplicity adjusted p-value.

Another aspect of the invention includes a method of testing food intolerance in patients diagnosed with or suspected to have irritable bowel syndrome. The method includes a step of contacting a food preparation with a bodily fluid of a patient that is diagnosed with or suspected to have irritable bowel syndrome. The bodily fluid is associated with a gender identification. It is especially preferred that the step of contacting is performed under conditions that allow IgG from the bodily fluid to bind to at least one component of the food preparation. The method continues with a step of measuring IgG bound to the at least one component of the food preparation to obtain a signal, and then comparing the signal to a gender-stratified reference value for the food preparation using the gender identification to obtain a result. Then, the method also includes a step of updating or generating a report using the result.

Another aspect of the invention includes a method of generating a test for food intolerance in patients diagnosed with or suspected to have irritable bowel syndrome. The method includes a step of obtaining test results for a plurality of distinct food preparations. The test results are based on bodily fluids of patients diagnosed with or suspected to have irritable bowel syndrome and bodily fluids of a control group not diagnosed with or not suspected to have irritable bowel syndrome. The method also includes a step of stratifying the test results by gender for each of the distinct food preparations. Then the method continues with a step of assigning for a predetermined percentile rank a different cutoff value for male and female patients for each of the distinct food preparations.

Still another aspect of the invention includes a use of a plurality of distinct food preparations coupled to individually addressable respective solid carriers in a diagnosis of irritable bowel syndrome. The plurality of distinct food preparations are selected based on their average discriminatory p-value of ≤0.07 as determined by raw p-value or an average discriminatory p-value of ≤0.10 as determined by FDR multiplicity adjusted p-value.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

Table 1 shows a list of food items from which food preparations can be prepared.

Table 2 shows statistical data of foods ranked according to 2-tailed FDR multiplicity-adjusted p-values.

Table 3 shows statistical data of ELISA score by food and gender.

Table 4 shows cutoff values of foods for a predetermined percentile rank.

Figure 1A:
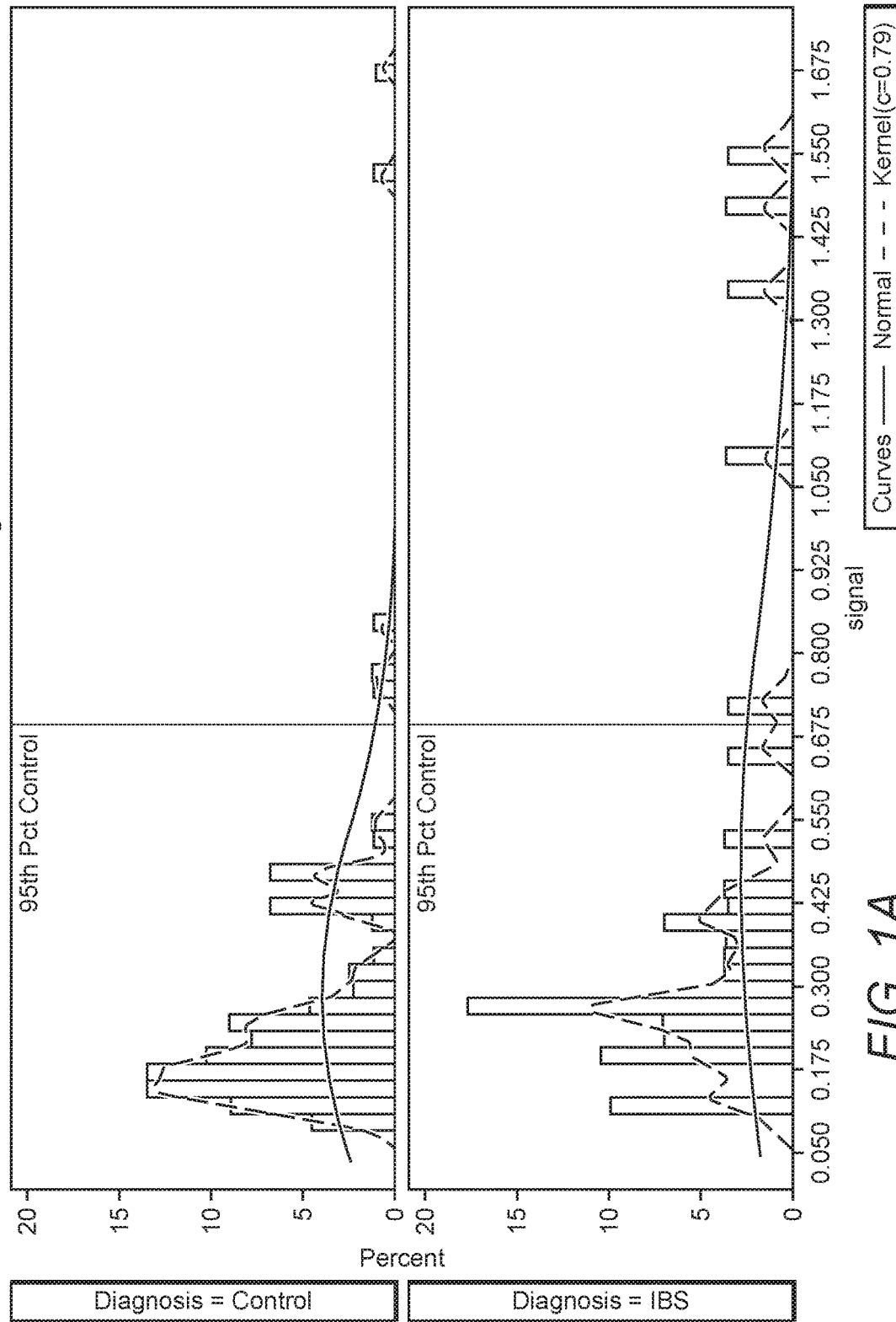

FIG. 1A illustrates ELISA signal score of male IBS patients and control tested with white wheat.

FIG. 1B illustrates a distribution of percentage of male IBS subjects exceeding the $90^{th}$ and $95^{th}$ percentile tested with white wheat.

Figure 1C:
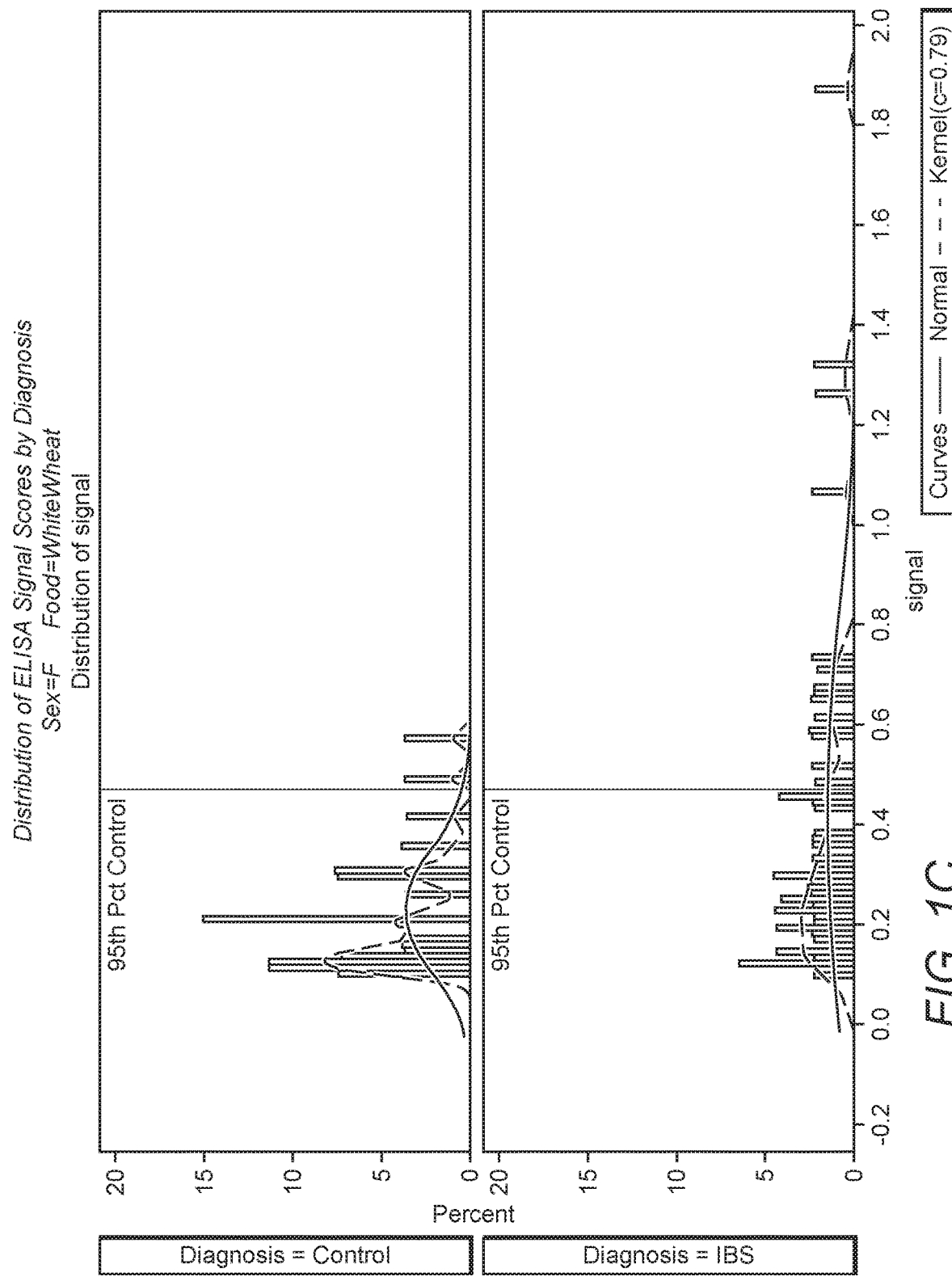

FIG. 1C illustrates a signal distribution in women along with the $95^{th}$ percentile cutoff as determined from the female control population tested with white wheat.

FIG. 1D illustrates a distribution of percentage of female IBS subjects exceeding the $90^{th}$ and $95^{th}$ percentile tested with white wheat.

Figure 2A:
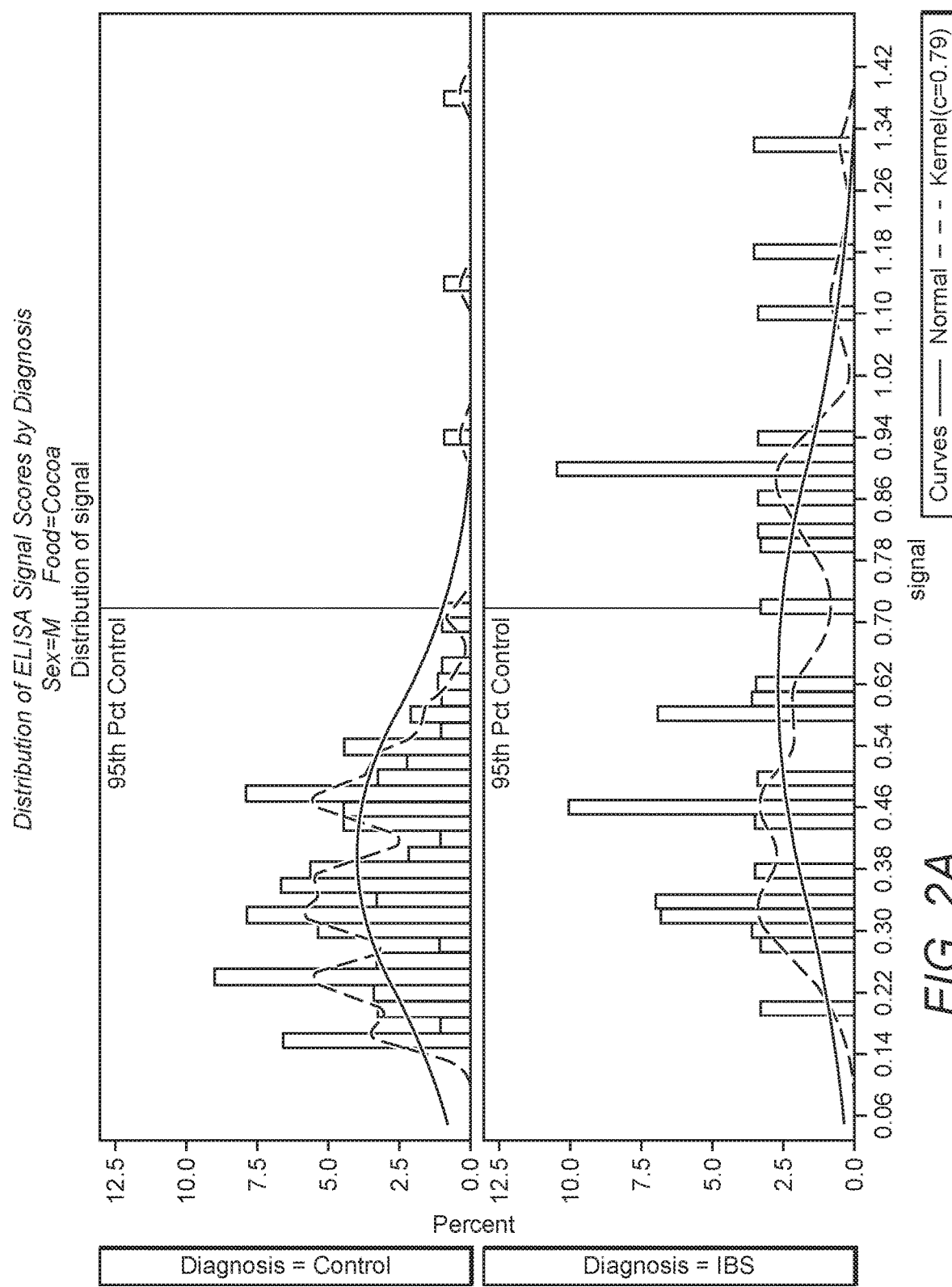

FIG. 2A illustrates ELISA signal score of male IBS patients and control tested with cocoa.

Figure 2B:
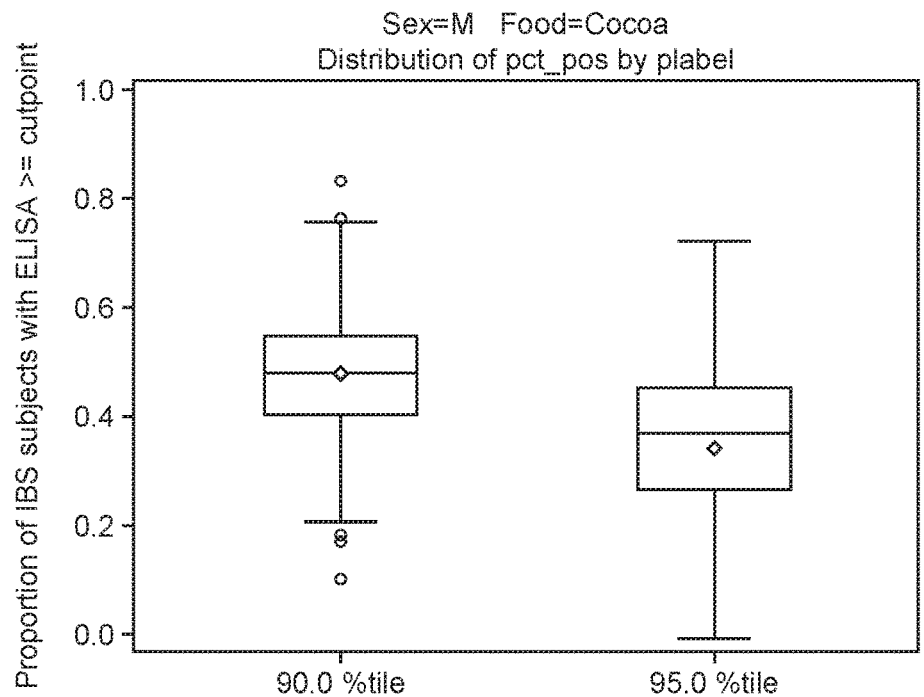

FIG. 2B illustrates a distribution of percentage of male IBS subjects exceeding the $90^{th}$ and $95^{th}$ percentile tested with cocoa.

Figure 2D:
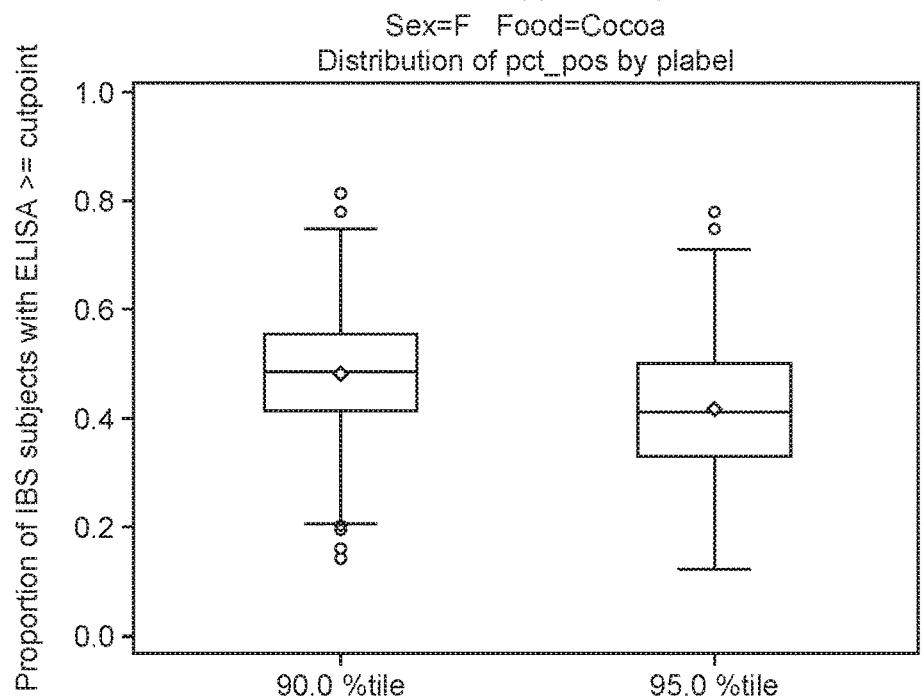
Figure 2C:
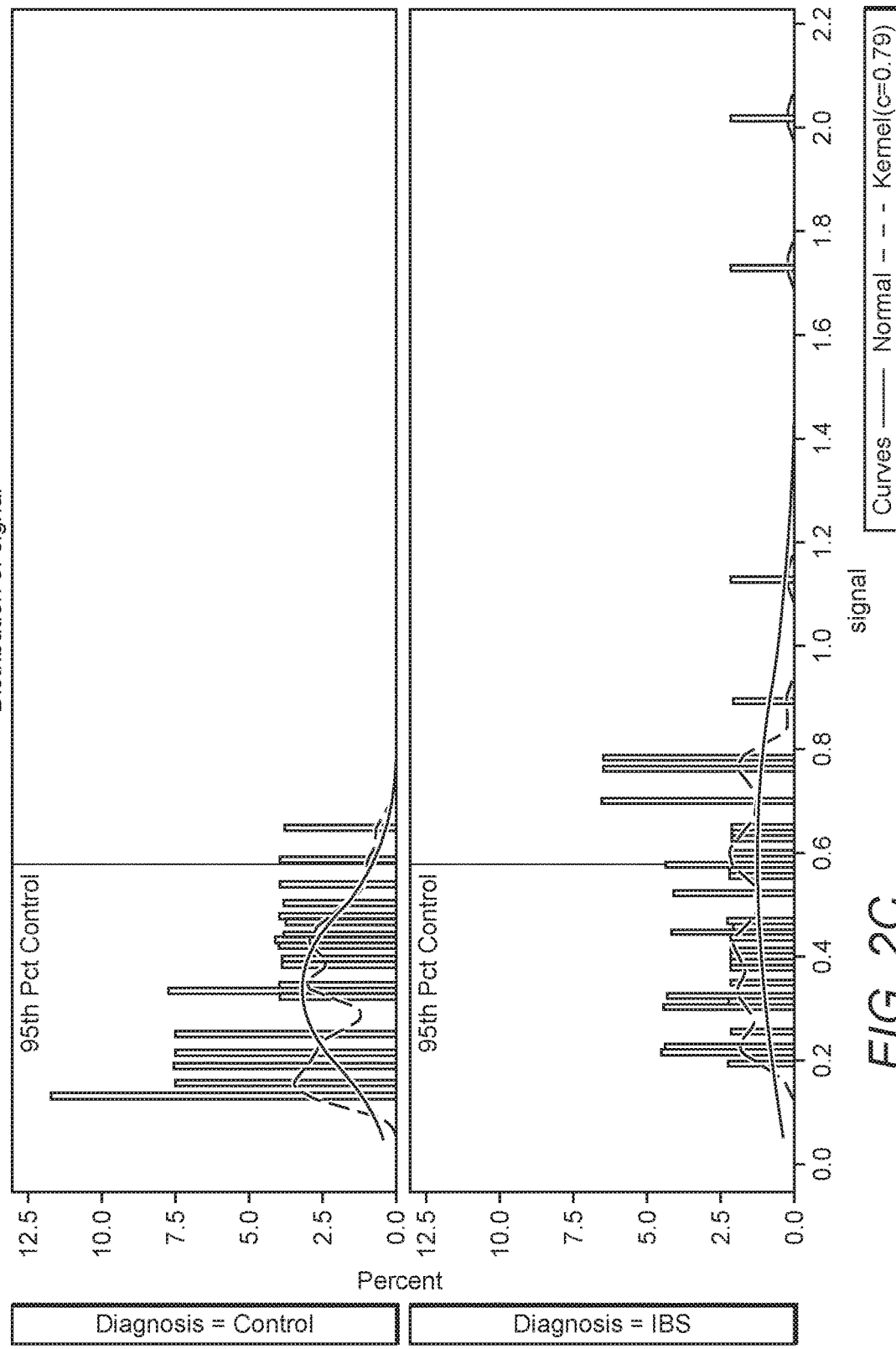

FIG. 2C illustrates a signal distribution in women along with the $95^{th}$ percentile cutoff as determined from the female control population tested with cocoa.

FIG. 2D illustrates a distribution of percentage of female IBS subjects exceeding the $90^{th}$ and $95^{th}$ percentile tested with cocoa.

Figure 3A:
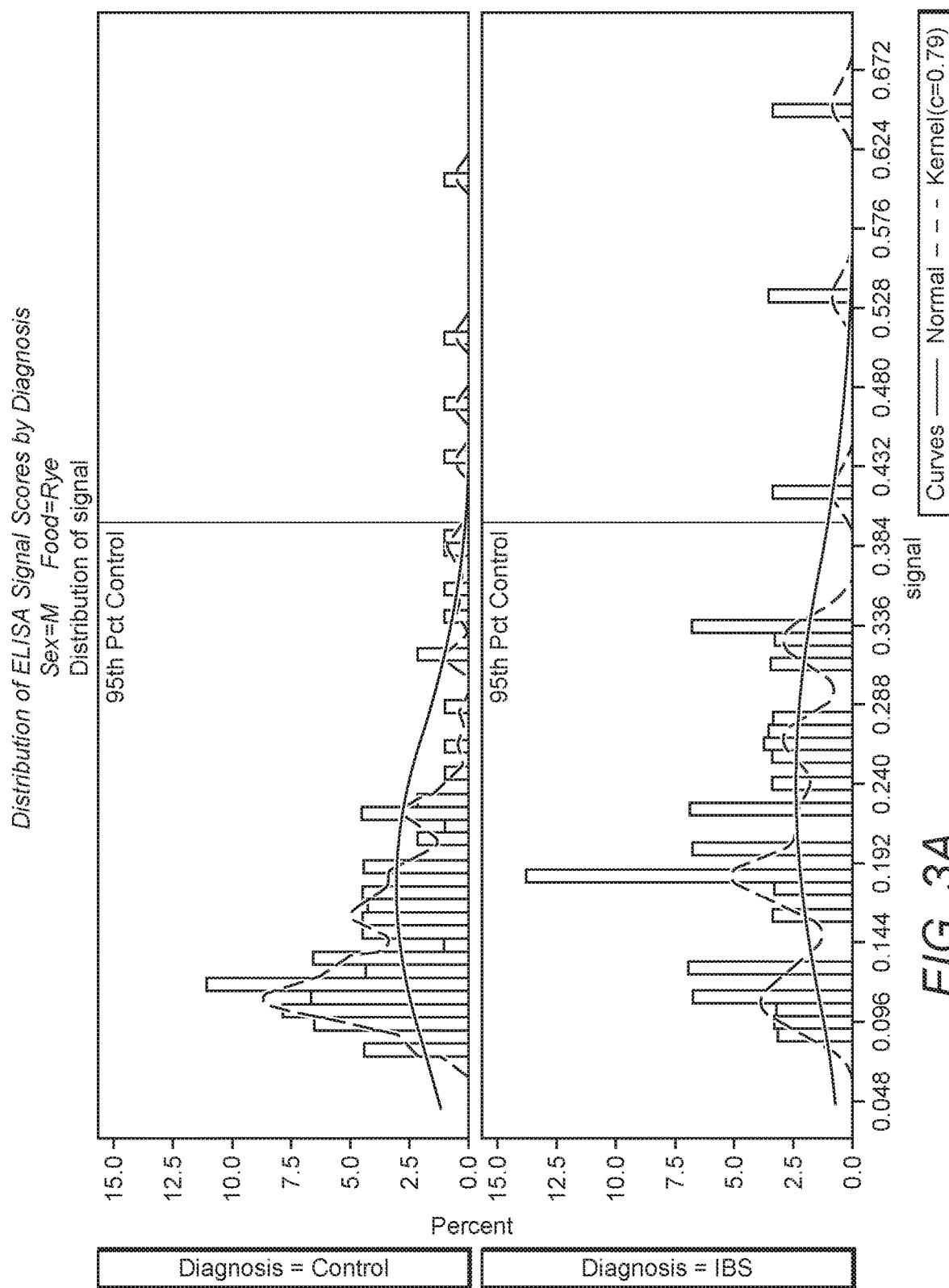

FIG. 3A illustrates ELISA signal score of male IBS patients and control tested with rye.

FIG. 3B illustrates a distribution of percentage of male IBS subjects exceeding the $90^{th}$ and $95^{th}$ percentile tested with rye.

Figure 3C:
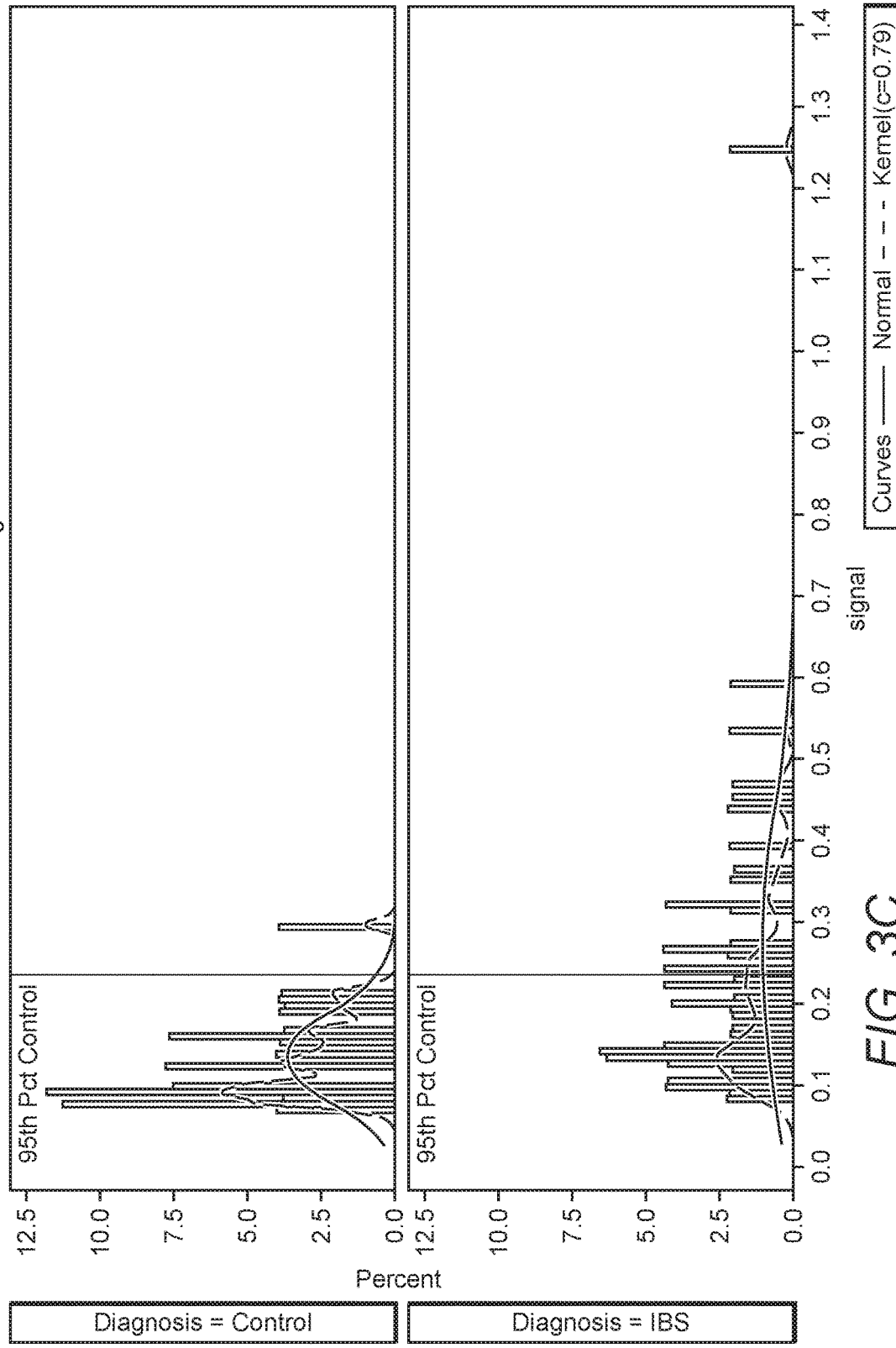

FIG. 3C illustrates a signal distribution in women along with the $95^{th}$ percentile cutoff as determined from the female control population tested with rye.

FIG. 3D illustrates a distribution of percentage of female IBS subjects exceeding the $90^{th}$ and $95^{th}$ percentile tested with rye.

Figure 4A:
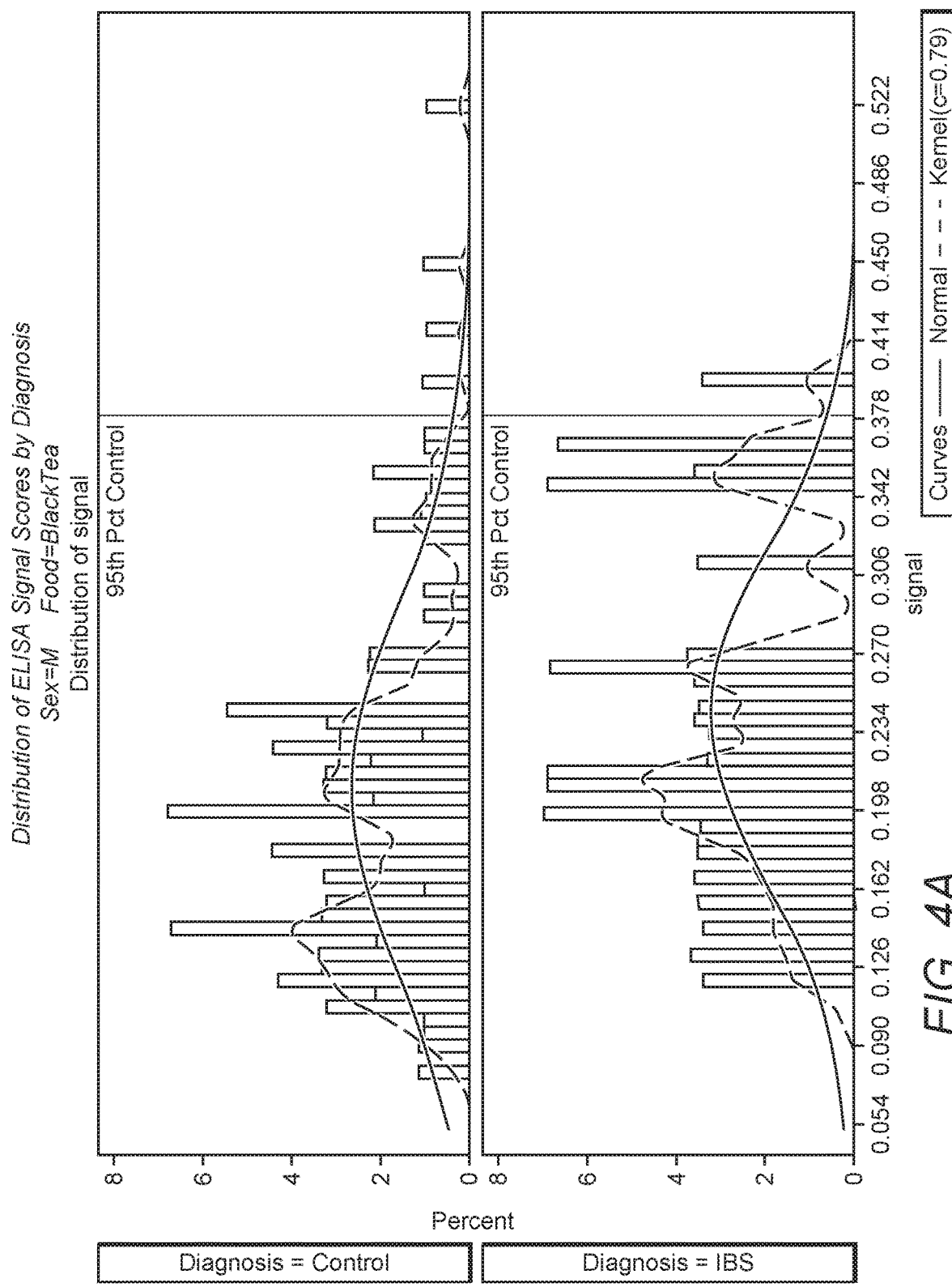

FIG. 4A illustrates ELISA signal score of male MS patients and control tested with black tea.

Figure 4B:
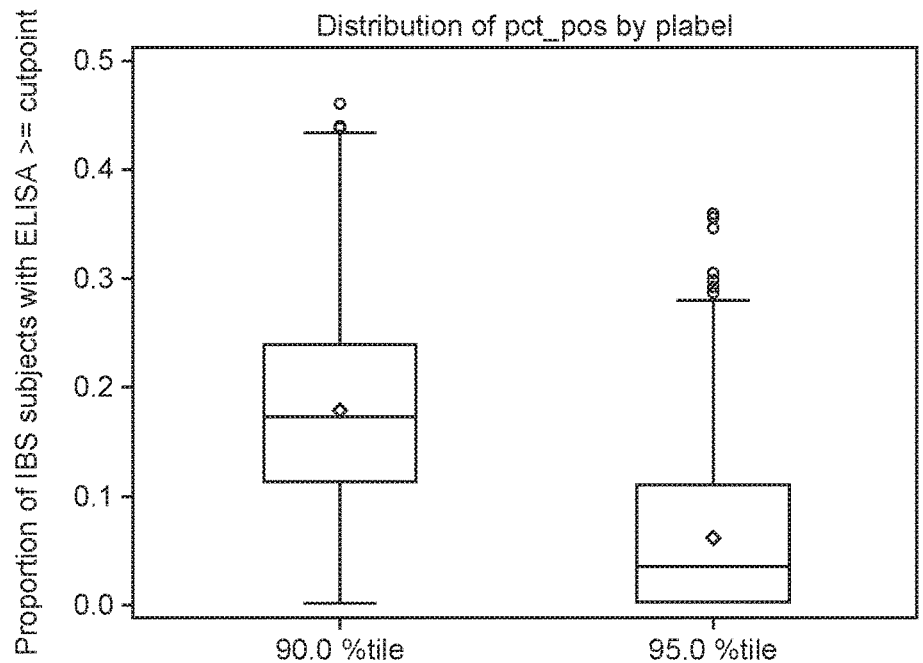

FIG. 4B illustrates a distribution of percentage of male IBS subjects exceeding the $90^{th}$ and $95^{th}$ percentile tested with black tea.

Figure 4D:
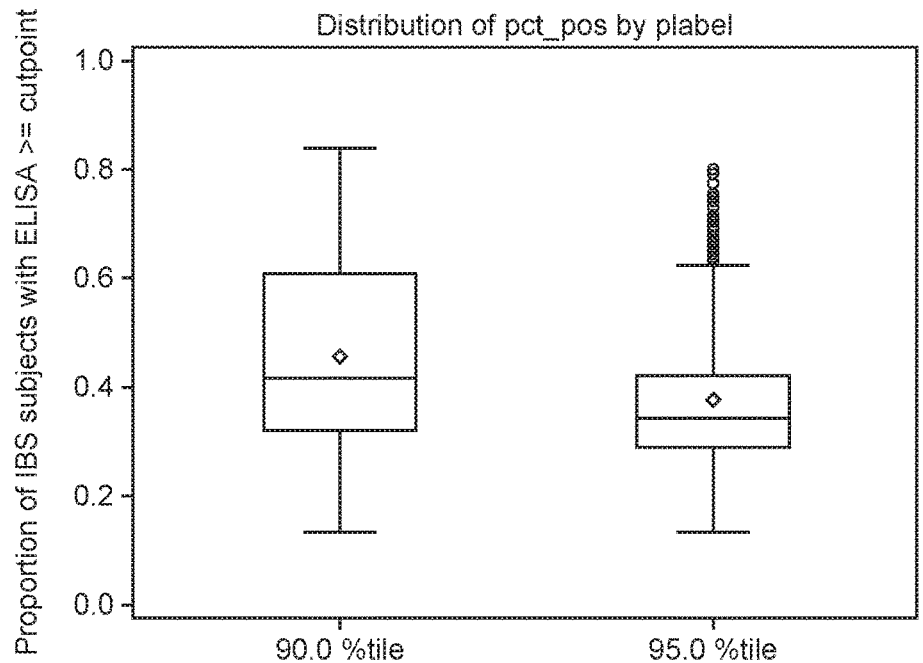
Figure 4C:
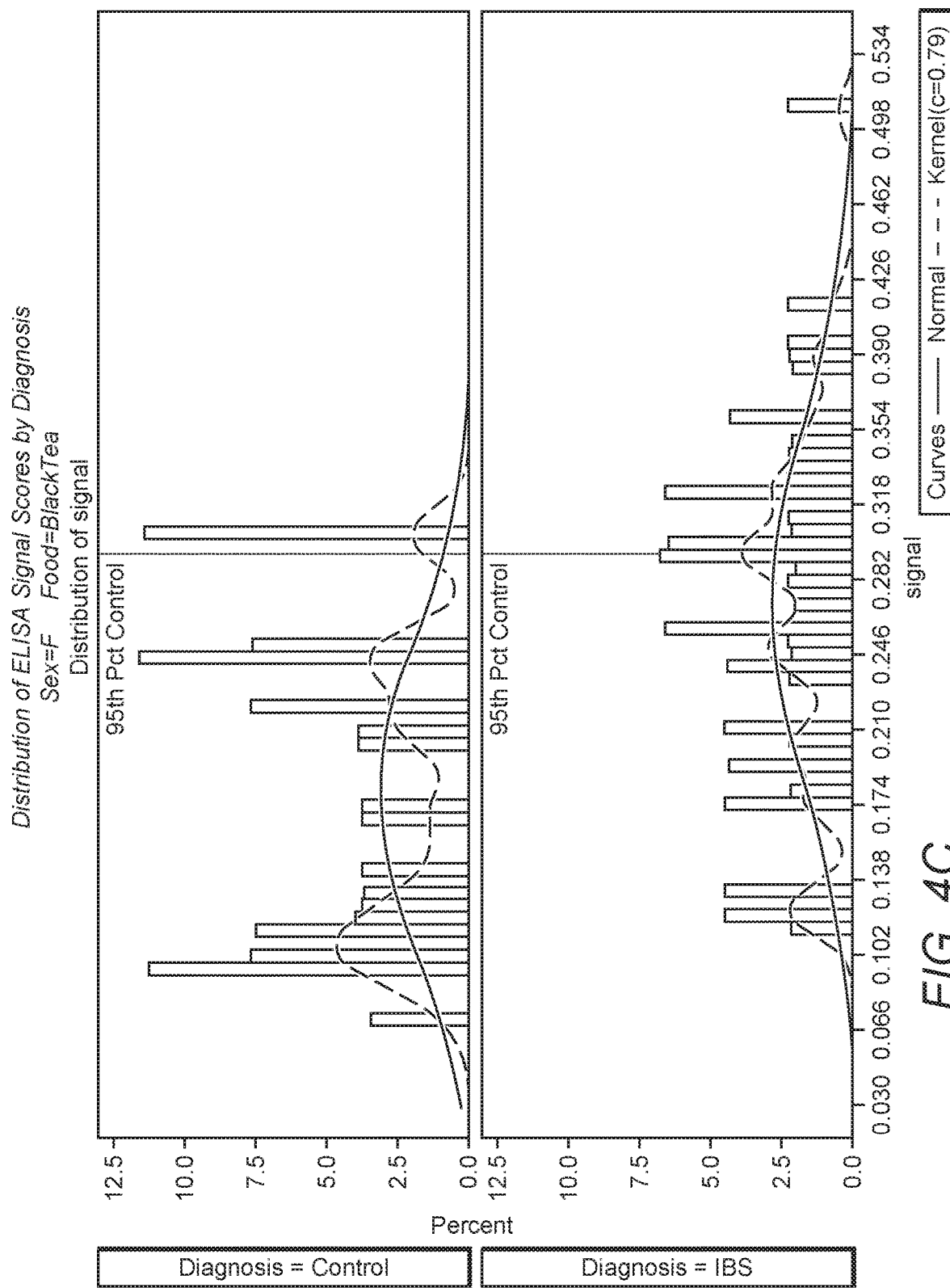

FIG. 4C illustrates a signal distribution in women along with the $95^{th}$ percentile cutoff as determined from the female control population tested with black tea.

FIG. 4D illustrates a distribution of percentage of female IBS subjects exceeding the $90^{th}$ and $95^{th}$ percentile tested with black tea.

FIGS. 5A-5B illustrate distributions of IBS subjects by number of foods that were identified as trigger foods at the $90^{th}$ percentile and $95^{th}$ percentile.

Table 5 shows raw data of IBS patients and control with number of positive results based on the $90^{th}$ percentile.

Table 6 shows statistical data summarizing the raw data of IBS patient populations shown in Table 5.

Table 7 shows statistical data summarizing the raw data of control populations shown in Table 5.

Table 8 shows statistical data summarizing the raw data of IBS patient populations shown in Table 5 transformed by logarithmic transformation.

Table 9 shows statistical data summarizing the raw data of control populations shown in Table 5 transformed by logarithmic transformation.

Table 10 shows statistical data of an independent T-test to compare the geometric mean number of positive foods between the IBS and non-IBS samples.

Table 11 shows statistical data of a Mann-Whitney test to compare the geometric mean number of positive foods between the IBS and non-IBS samples.

Figure 6A:
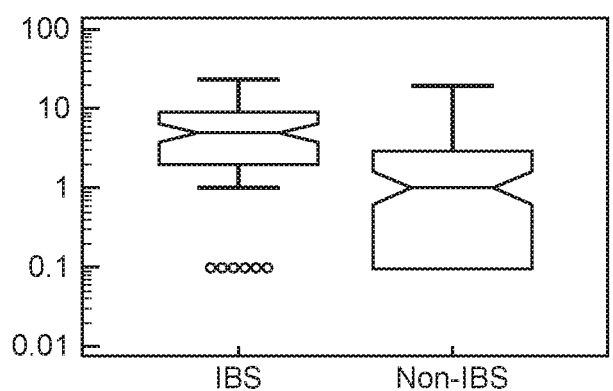

FIG. 6A illustrates a box and whisker plot of data shown in Table 5.

Figure 6B:
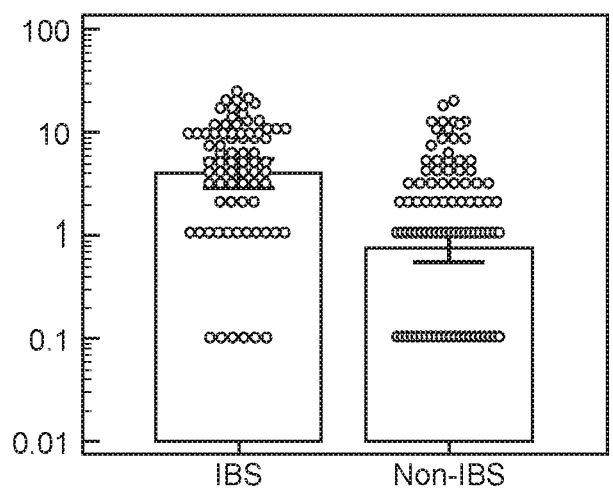

FIG. 6B illustrates a notched box and whisker plot of data shown in Table 5.

Figure 7:
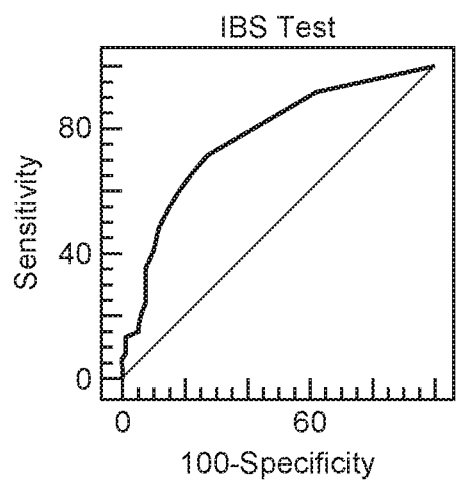

FIG. 7 illustrates the ROC curve corresponding to the statistical data shown in Table 12.

Table 12 shows statistical data of a Receiver Operating Characteristic (ROC) curve analysis of data shown in Tables 5-11.

Table 13 shows statistical data of performance metrics in predicting IBS status among female patients from number of positive foods.

Table 14 shows statistical data of performance metrics in predicting MS status among male patients from number of positive foods.

DETAILED DESCRIPTION

The inventors have discovered that food preparations used in food tests to identify trigger foods in patients diagnosed with or suspected to have IBS are not equally well predictive and/or associated with IBS/IBS symptoms. Indeed, various experiments have revealed that among a wide variety of food items certain food items are highly predictive/associated with IBS whereas others have no statistically significant association with IBS.

Even more unexpectedly, the inventors discovered that in addition to the high variability of food items, gender variability with respect to response in a test plays a substantial role in the determination of association or a food item with IBS. Consequently, based on the inventors' findings and further contemplations, test kits and methods are now presented with substantially higher predictive power in the choice of food items that could be eliminated for reduction of MS signs and symptoms.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In one especially preferred aspect, the inventors therefore contemplate a test kit or test panel that is suitable for testing food intolerance in patients where the patient is diagnosed with or suspected to have irritable bowel syndrome. Most preferably, such test kit or panel will include a plurality of distinct food preparations (e.g., raw or processed extract, preferably aqueous extract with optional co-solvent, which may or may not be filtered) that are coupled to individually addressable respective solid carriers (e.g., in a form of an array or a micro well plate), wherein the distinct food preparations have an average discriminatory p-value of ≤0.07 as determined by raw p-value or an average discriminatory p-value of ≤0.10 as determined by FDR multiplicity adjusted p-value. As used herein, processed extracts includes food extracts made of food items that are mechanically or chemically modified (e.g., minced, heated, boiled, fermented, smoked, etc.).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

While not limiting to the inventive subject matter, food preparations will typically be drawn from foods generally known or suspected to trigger signs or symptoms of IBS. Particularly suitable food preparations may be identified by the experimental procedures outlined below. Thus, it should be appreciated that the food items need not be limited to the items described herein, but that all items are contemplated that can be identified by the methods presented herein. Therefore, exemplary food preparations include at least two, at least four, at least eight, or at least 12 food preparations prepared from cocoa, tea (e.g. green, black, etc.), oat, cabbage, cow milk, onion (e.g. yellow, white, maui, etc.), honey, rye, corn, yeast, wheat (e.g. red, white, etc.), soybean, egg, tuna, lemon, pineapple, cucumber, orange, halibut, walnut, grapefruit, cane sugar, chicken, blueberry, or shrimp (e.g. US Gulf white, Thai, Tiger, etc.). Additionally contemplated food preparations are prepared from Crab (e.g. Dungeness, Blue, Alaskan King, etc.), Barley, Strawberry, Pork, Rice (e.g. Brown, White, etc.), Beef, Cashew, Codfish, Potato, White Sesame, Broccoli, Almond, Turkey, Scallop, and/or Salmon. Still further especially contemplated food items and food additives from which food preparations can be prepared are listed in Table 1.

Using bodily fluids from patients diagnosed with or suspected to have irritable bowel syndrome and healthy control group individuals (i.e., those not diagnosed with or not suspected to have irritable bowel syndrome), numerous additional food items may be identified. Preferably, such identified food items will have high discriminatory power and as such have a p-value of ≤0.15, more preferably ≤0.10, and most preferably ≤0.05 as determined by raw p-value, and/or a p-value of ≤0.10, more preferably ≤0.08, and most preferably ≤0.07 as determined by False Discovery Rate (FDR) multiplicity adjusted p-value.

Therefore, where a panel has multiple food preparations, it is contemplated that the plurality of distinct food preparations has an average discriminatory p-value of ≤0.05 as determined by raw p-value or an average discriminatory p-value of ≤0.08 as determined by FDR multiplicity adjusted p-value, or even more preferably an average discriminatory p-value of ≤0.025 as determined by raw p-value or an average discriminatory p-value of ≤0.07 as determined by FDR multiplicity adjusted p-value. In further preferred aspects, it should be appreciated that the FDR multiplicity adjusted p-value may be adjusted for at least one of age and gender, and most preferably adjusted for both age and gender. On the other hand, where a test kit or panel is stratified for use with a single gender, it is also contemplated that in a test kit or panel at least 50% (and more typically 70% or all) of the plurality of distinct food preparations, when adjusted for a single gender, have an average discriminatory p-value of ≤0.07 as determined by raw p-value or an average discriminatory p-value of ≤0.10 as determined by FDR multiplicity adjusted p-value. Furthermore, it should be appreciated that other stratifications (e.g., dietary preference, ethnicity, place of residence, genetic predisposition or family history, etc.) are also contemplated, and the PHOSITA will be readily appraised of the appropriate choice of stratification.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Of course, it should be noted that the particular format of the test kit or panel may vary considerably and contemplated formats include micro well plates, a microfluidic device, dip sticks, membrane-bound arrays, etc. Consequently, the solid carrier to which the food preparations are coupled may include wells of a multiwall plate, a microfluidic device, a (e.g., color-coded or magnetic) bead, or an adsorptive film (e.g., nitrocellulose or micro/nanoporous polymeric film), a chemical sensor, or an electrical sensor, (e.g. a printed copper sensor or microchip). In some embodiments, it is also contemplated that a suitable solid carrier for molecular absorption and signal detection by a light detector (e.g., surface plasmon resonance, etc.) can be used.

Consequently, the inventors also contemplate a method of testing food intolerance in patients that are diagnosed with or suspected to have irritable bowel syndrome. Most typically, such methods will include a step of contacting a food preparation with a bodily fluid (e.g., whole blood, plasma, serum, saliva, or a fecal suspension) of a patient that is diagnosed with or suspected to have irritable bowel syndrome, and wherein the bodily fluid is associated with a gender identification. As noted before, the step of contacting is preferably performed under conditions that allow IgG (or IgE or IgA or IgM) from the bodily fluid to bind to at least one component of the food preparation, and the IgG bound to the component(s) of the food preparation are then quantified/measured to obtain a signal. Most preferably, the signal is then compared against a gender-stratified reference value (e.g., at least a 90th percentile value) for the food preparation using the gender identification to obtain a result, which is then used to update or generate a report. Preferably, the report can be generated as an aggregate result of individual assay results.

Most commonly, such methods will not be limited to a single food preparation, but will employ multiple different food preparations. As noted before, suitable food preparations can be identified using various methods as described below, however, especially preferred food preparations include cocoa, tea (e.g. green, black, etc.), oat, cabbage, cow milk, onion (e.g. yellow, white, maui, etc.), honey, rye, corn, yeast, wheat (e.g. red, white, etc.), soybean, egg, tuna, lemon, pineapple, cucumber, orange, halibut, walnut, grapefruit, cane sugar, chicken, blueberry, or shrimp (e.g. US Gulf white, Thai, Tiger, etc.). Additionally contemplated food preparations are prepared from Crab (e.g. Dungeness, Blue, Alaskan King, etc.), Barley, Strawberry, Pork, Rice (e.g. Brown, White, etc.), Beef, Cashew, Codfish, Potato, White Sesame, Broccoli, Almond, Turkey, Scallop, and/or Salmon, and/or items of Table 1. As also noted above, it is generally preferred that at least some, or all of the different food preparations have an average discriminatory p-value of ≤0.07 (or ≤0.05, or ≤0.025) as determined by raw p-value, and/or or an average discriminatory p-value of ≤0.10 (or ≤0.08, or ≤0.07) as determined by FDR multiplicity adjusted p-value.

While it is preferred that food preparations are prepared from a single food items as crude extracts, or crude filtered extracts, it is contemplated that food preparations can be prepared from mixtures of a plurality of food items (e.g. a mixture of citrus comprising lemon, orange and lime, a mixture of crabs comprising blue crab, king crab and Dungeness crab, a mixture of wheat comprising a white wheat and red wheat, a mixture of shrimp comprising US Gulf white, Thai and Tiger shrimps, etc). In some embodiments, it is also contemplated that food preparations can be prepared from purified food antigens or recombinant food antigens.

As it is generally preferred that the food preparation is immobilized on a solid surface (typically in an addressable manner), it is contemplated that the step of measuring the IgG or other type of antibody bound to the component of the food preparation is performed via an immunoassay test (e.g., ELISA test, antibody capture enzyme immunoassay, other types of antibody capture assays, etc.)

Viewed from a different perspective, the inventors also contemplate a method of generating a test for food intolerance in patients diagnosed with or suspected to have irritable bowel syndrome. Because the test is applied to patients already diagnosed with or suspected to have irritable bowel syndrome, the authors do not contemplate that the method has a primary diagnostic purpose for IBS. Instead, the method is for identifying triggering food items among already diagnosed or suspected IBS patients. Such test will typically include a step of obtaining one or more test results (e.g., ELISA, antibody capture enzyme immunoassay) for various distinct food preparations, wherein the test results are based on bodily fluids (e.g., blood saliva, fecal suspension) of patients diagnosed with or suspected to have irritable bowel syndrome and bodily fluids of a control group not diagnosed with or not suspected to have irritable bowel syndrome. Most preferably, the test results are then stratified by gender for each of the distinct food preparations, a different cutoff value for male and female patients for each of the distinct food preparations (e.g., cutoff value for male and female patients has a difference of at least 10% (abs)) is assigned for a predetermined percentile rank (e.g., 90th or 95th percentile).

As noted earlier, and while not limiting to the inventive subject matter, it is contemplated that the distinct food preparations include at least two (or six, or ten, or 15) food preparations prepared from food items selected from the group consisting of cocoa, tea (e.g. green, black, etc.), oat, cabbage, cow milk, onion (e.g. yellow, white, maui, etc.), honey, rye, corn, yeast, wheat (e.g. red, white, etc.), soybean, egg, tuna, lemon, pineapple, cucumber, orange, halibut, walnut, grapefruit, cane sugar, chicken, blueberry, or shrimp (e.g. US Gulf white, Thai, Tiger, etc.). Additionally contemplated food preparations are prepared from Crab (e.g. Dungeness, Blue, Alaskan King, etc.), Barley, Strawberry, Pork, Rice (e.g. Brown, White, etc.), Beef, Cashew, Codfish, Potato, White Sesame, Broccoli, Almond, Turkey, Scallop, and/or Salmon, and/or items of Table 1. On the other hand, where new food items are tested, it should be appreciated that the distinct food preparations include a food preparation prepared from a food items other than cocoa, tea (e.g. green, black, etc.), oat, cabbage, cow milk, onion (e.g. yellow, white, maui, etc.), honey, rye, corn, yeast, wheat (e.g. red, white, etc.), soybean, egg, tuna, lemon, pineapple, cucumber, orange, halibut, walnut, grapefruit, cane sugar, chicken, blueberry, or shrimp (e.g. US Gulf white, Thai, Tiger, etc.). Regardless of the particular choice of food items, it is generally preferred however, that the distinct food preparations have an average discriminatory p-value of ≤0.07 (or ≤0.05, or ≤0.025) as determined by raw p-value or an average discriminatory p-value of ≤0.10 (or ≤0.08, or ≤0.07) as determined by FDR multiplicity adjusted p-value. Exemplary aspects and protocols, and considerations are provided in the experimental description below.

Thus, it should be appreciated that by having a high-confidence test system as described herein, the rate of false-positive and false negatives can be significantly reduced, and especially where the test systems and methods are gender stratified or adjusted for gender differences as shown below. Such advantages have heretofore not been realized and it is expected that the systems and methods presented herein will substantially increase the predictive power of food sensitivity tests for patients diagnosed with or suspected to have IBS.

Experiments

General Protocol for Food Preparation Generation:

Commercially available food extracts (available from Biomerica Inc., 17571 Von Karman Ave, Irvine, Calif. 92614) prepared from the edible portion of the respective raw foods were used to prepare ELISA plates following the manufacturer's instructions.

For some food extracts, the inventors found that food extracts prepared with specific procedures to generate food extracts provides more superior results in detecting elevated IgG reactivity in IBS patients compared to commercially available food extracts. For example, for grains and nuts, a three-step procedure of generating food extracts is preferred. The first step is a defatting step. In this step, lipids from grains and nuts are extracted by contacting the flour of grains and nuts with a non-polar solvent and collecting residue. Then, the defatted grain or nut flour are extracted by contacting the flour with elevated pH to obtain a mixture and removing the solid from the mixture to obtain the liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at −70° C. and multiple freeze-thaws without a loss of activity.

For another example, for meats and fish, a two step procedure of generating food extract is preferred. The first step is an extraction step. In this step, extracts from raw, uncooked meats or fish are generated by emulsifying the raw, uncooked meats or fish in an aqueous buffer formulation in a high impact pressure processor. Then, solid materials are removed to obtain liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at −70° C. and multiple freeze-thaws without a loss of activity.

For still another example, for fruits and vegetables, a two step procedure of generating food extract is preferred. The first step is an extraction step. In this step, liquid extracts from fruits or vegetables are generated using an extractor (e.g., masticating juicer, etc) to pulverize foods and extract juice. Then, solid materials are removed to obtain liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at −70° C. and multiple freeze-thaws without a loss of activity.

Blocking of ELISA Plates:

To optimize signal to noise, plates were blocked with a proprietary blocking buffer. In a preferred embodiment, the blocking buffer includes 20-50 mM of buffer from 4-9 pH, a protein of animal origin and a short chain alcohol. Other blocking buffers, including several commercial preparations, were attempted but could not provide adequate signal to noise and low assay variability required.

ELISA Preparation and Sample Testing:

Food antigen preparations were immobilized onto respective microtiter wells following the manufacturer's instructions. For the assays, the food antigens were allowed to react with antibodies present in the patients' serum, and excess serum proteins were removed by a wash step. For detection of IgG antibody binding, enzyme labeled anti-IgG antibody conjugate was allowed to react with antigen-antibody complex. A color was developed by the addition of a substrate that reacts with the coupled enzyme. The color intensity was measured and is directly proportional to the concentration of IgG antibody specific to a particular food antigen.

Methodology to Determine Ranked Food List in Order of Ability of ELISA Signals to Distinguish IBS from Control Subjects:

Out of an initial selection (e.g., 100 food items, or 150 food items, or even more), samples can be eliminated prior to analysis due to low consumption in an intended population. In addition, specific food items can be used as being representative of the a larger more generic food group, especially where prior testing has established a correlation among different species within a generic group (most preferably in both genders, but also suitable for correlation for a single gender). For example, Thailand Shrimp could be dropped in favor of U.S. Gulf White Shrimp as representative of the "shrimp" food group, or King Crab could be dropped in favor of Dungeness Crab as representative of the "crab" food group In further preferred aspects, the final list foods is shorter than 50 food items, and more preferably equal or less than of 40 food items.

Since the foods ultimately selected for the food intolerance panel will not be specific for a particular gender, a gender-neutral food list was necessary. Since the observed sample was imbalanced by gender (e.g., Controls: 22% female, IBS: 64% female), differences in ELISA signal magnitude strictly due to gender were removed by modeling signal scores against gender using a two-sample t-test and storing the residuals for further analysis. For each of the tested foods, residual signal scores were compared between IBS and controls using a permutation test on a two-sample t-test with 50,000 resamplings. The Satterthwaite approximation was used for the denominator degrees of freedom to account for lack of homogeneity of variances, and the 2-tailed permuted p-value represented the raw p-value for each food. False Discovery Rates (FDR) among the comparisons, were adjusted by any, acceptable statistical procedures (e.g., Benjamini-Hochberg, Family-wise Error Rate (FWER), Per Comparison Error Rate (PCER), etc.).

Foods were then ranked according to their 2-tailed FDR multiplicity-adjusted p-values. Foods with adjusted p-values equal to or lower than the desired FDR threshold were deemed to have significantly higher signal scores among IBS than control subjects and therefore deemed candidates for inclusion into a food intolerance panel. A typical result that is representative of the outcome of the statistical procedure is provided in Table 2. Here the ranking of foods is according to 2-tailed permutation T-test p-values with FDR adjustment.

Notably, the inventors discovered that even for the same food preparation tested, the ELISA score for at least several food items varied dramatically, and exemplary raw data are provided in Table 3. As will be readily appreciated, data unstratified by gender will therefore lose significant explanatory power where the same cutoff value is applied to raw data for male and female data. To overcome such disadvantage, the inventors stratified the data by gender as described below.

Statistical Method for Cutpoint Selection for Each Food:

The determination of what ELISA signal scores would constitute a "positive" response was made by summarizing the distribution of signal scores among the Control subjects. For each food, IBS subjects who had have observed scores greater than or equal to selected quantiles of the Control subject distribution were deemed "positive". To attenuate the influence of any one subject on cutpoint determination, each food-specific and gender-specific dataset was bootstrap resampled 1000 times. Within each bootstrap replicate, the 90th and 95th percentiles of the Control signal scores were determined. Each IBS subject in the bootstrap sample was compared to the 90th and 95% percentiles to determine whether he/she had a "positive" response. The final 90th and 95th percentile-based cutpoints for each food and gender were computed as the average 90th and 95th percentiles across the 1000 samples. The number of foods for which each IBS subject was rated as "positive" was computed by pooling data across foods: Using such method, the inventors were now able to identify cutoff values for a predetermined percentile rank that in most cases was substantially different as can be taken from Table 4.

Typical examples for the gender difference in IgG response in blood with respect to wheat is shown in FIGS. 1A-1D, where FIG. 1A shows the signal distribution in men along with the $95^{th}$ percentile cutoff as determined from the male control population. FIG. 1B shows the distribution of percentage of male IBS subjects exceeding the $90^{th}$ and $95^{th}$ percentile, while FIG. 1C shows the signal distribution in women along with the $95^{th}$ percentile cutoff as determined from the female control population. FIG. 1D shows the distribution of percentage of female IBS subjects exceeding the $90^{th}$ and $95^{th}$ percentile. In the same fashion, FIGS. 2A-2D exemplarily depict the differential response to cocoa, FIGS. 3A-3D exemplarily depict the differential response to rye, and FIGS. 4A-4D exemplarily depict the differential response to black tea. FIGS. 5A-5B show the distribution of IBS subjects by number of foods that were identified as trigger foods at the $90^{th}$ percentile (5A) and $95^{th}$ percentile (5B). Inventors contemplate that regardless of the particular food items, male and female responses were notably distinct.

It should be noted that nothing in the art have provided any predictable food groups related to IBS that is gender-stratified. Thus, a discovery of food items that show distinct responses by gender is a surprising result, which could not be obviously expected in view of all previously available arts. In other words, selection of food items based on gender stratification provides an unexpected technical effect such that statistical significances for particular food items as triggering food among male or female IBS patients have been significantly improved.

Normalization of IgG Response Data:

While the raw data of the patient's IgG response results can be use to compare strength of response among given foods, it is also contemplated that the IgG response results of a patient are normalized and indexed to generate unit-less numbers for comparison of relative strength of response to a given food. For example, one or more of a patient's food specific IgG results (e.g., IgG specific to Dungeness crab and IgG specific to egg) can be normalized to the patient's total IgG. The normalized value of the patient's IgG specific to Dungeness crab can be 0.1 and the normalized value of the patient's IgG specific to egg can be 0.3. In this scenario, the relative strength of the patient's response to egg is three times higher compared to Dungeness crab. Then, the patient's sensitivity to egg and Dungeness crab can be indexed as such.

In other examples, one or more of a patient's food specific IgG results (e.g., IgG specific to shrimp and IgG specific to pork) can be normalized to the global mean of that patient's food specific IgG results. The global means of the patient's food specific IgG can be measured by total amount of the patient's food specific IgG. In this scenario, the patient's specific IgG to shrimp can be normalized to the mean of patient's total food specific IgG (e.g., mean of IgG levels to shrimp, pork, Dungeness crab, chicken, peas, etc.). However, it is also contemplated that the global means of the patient's food specific IgG can be measured by the patient's IgG levels to a specific type of food via multiple tests. If the patient have been tested for his sensitivity to shrimp five times and to pork seven times previously, the patient's new IgG values to shrimp or to pork are normalized to the mean of five-times test results to shrimp or the mean of seven-times test results to pork. The normalized value of the patient's IgG specific to shrimp can be 6.0 and the normalized value of the patient's IgG specific to pork can be 1.0. In this scenario, the patient has six times higher sensitivity to shrimp at this time compared to his average sensitivity to shrimp, but substantially similar sensitivity to pork. Then, the patient's sensitivity to shrimp and pork can be indexed based on such comparison.

Methodology to Determine the Subset of IBS Patients with Food Sensitivities that Underlie IBS:

While it is suspected that food sensitivities plays a substantial role in signs and symptoms of IBS, some IBS patients may not have food sensitivities that underlie IBS. Those patients would not be benefit from dietary intervention to treat signs and symptoms of IBS. To determine the subset of such patients, body fluid samples of IBS patients and non-IBS patients can be tested with ELISA test using test devices with 24 food samples.

Table 5 provides exemplary raw data. As should be readily appreciated, data indicates number of positive results out of 24 sample foods based on $90^{th}$ percentile value. From the raw data shown in Table 5, average and standard deviation of the number of positive foods was computed for IBS and non-IBS patients. Additionally, the number and percentage of patients with zero positive foods was calculated for both IBS and non-IBS. The number and percentage of patients with zero positive foods is about 5 fold lower in the IBS population than in the non-IBS population (6% vs. 38%, respectively). Thus, it can be easily appreciated that the IBS patient having sensitivity to zero positive foods is unlikely to have food sensitivities underlying their signs and symptoms of IBS.

Table 6 and Table 7 show exemplary statistical data summarizing the raw data of two patient populations shown in Table 5. The statistical data includes normality, arithmetic mean, median, percentiles and 95% confidence interval (CI) for the mean and median representing number of positive foods in the MS population and the non-IBS population.

Table 8 and Table 9 show another exemplary statistical data summarizing the raw data of two patient populations shown in Table 5. In Tables 8 and 9, the raw data was transformed by logarithmic transformation to improve the data interpretation.

Table 10 and Table 11 show exemplary statistical data of an independent T-test (Table. 10, logarithmically transformed data) and a Mann-Whitney test (Table 11) to compare the geometric mean number of positive foods between the IBS and non-IBS samples. The data shown in Table 10 and Table 11 indicates statistically significant differences in the geometric mean of positive number of foods between the IBS population and the non-IBS population. In both statistical tests, it is shown that the number of positive responses with 24 food samples is significantly higher in the IBS population than in the non-IBS population with an average discriminatory p-value of ≤0.001. These statistical data is also illustrated as a box and whisker plot in FIG. 6A, and a notched box and whisker plot in FIG. 6B.

Table 12 shows exemplary statistical data of a Receiver Operating Characteristic (ROC) curve analysis of data shown in Tables 5-11 to determine the diagnostic power of the test used in Table 5 at discriminating IBS from non-IBS subjects. When a cutoff criterion of more than 2 positive foods is used, the test yields a data with 72.4% sensitivity and 72.2% specificity, with an area under the curve (AU-ROC) of 0.771. The p-value for the ROC is significant at a p-value of <0.0001. FIG. 7 illustrates the ROC curve corresponding to the statistical data shown in Table 12. Because the statistical difference between the IBS population and the non-IBS population is significant when the test results are cut off to positive number of 2, the number of foods that a patient tests positive could be used as a confirmation of the primary clinical diagnosis IBS, and whether it is likely that food sensitivities underlies on the patient's signs and symptoms of IBS. Therefore, the above test can be used as another 'rule in' test to add to currently available clinical criteria for diagnosis for IBS.

Method for Determining Distribution of Per-Person Number of Foods Declared "Positive":

To determine the distribution of number of "positive" foods per son and measure the diagnostic performance, the analysis was performed with 24 food items from the Table 1, which shows most positive responses to IBS patients. The 24 food items includes Cocoa, Black Tea, Oat, Cabbage, Cow's Milk, Yellow Onion, Honey, Rye, Corn, Yeast White Wheat, Soybean, Egg, Tuna, Lemon, Pineapple, Cucumber, Orange, Halibut, Walnut, Grapefruit, Cane Sugar, Chicken, US Gulf White Shrimp. To attenuate the influence of any one subject on this analysis, each food-specific and gender-specific dataset was bootstrap resampled 1000 times. Then, for each food item in the bootstrap sample, sex-specific cutpoint was determined using the 90th and 95th percentiles of the control population. Once the sex-specific cutpoints were determined, the sex-specific cutpoints was compared with the observed ELISA signal scores for both control and IBS subjects. In this comparison, if the observed signal is equal or more than the cutpoint value, then it is determined "positive" food, and if the observed signal is less than the cutpoint value, then it is determined "negative" food.

Once all food items were determined either positive or negative, the results of the 48 (24 foods×2 cutpoints) calls for each subject were saved within each bootstrap replicate. Then, for each subject, 24 calls were summed using $90^{th}$ percentile as cutpoint to get "Number of Positive Foods ($90^{th}$)," and the rest of 24 calls were summed using $95^{th}$ percentile to get "Number of Positive Foods ($95^{th}$)" Then, within each replicate, "Number of Positive Foods ($90^{th}$)" and "Number of Positive Foods ($95^{th}$)" were summarized across subjects to get descriptive statistics for each replicate as follows: 1) overall means equals to the mean of means, 2) overall standard deviation equals to the mean of standard deviations, 3) overall medial equals to the mean of medians, 4) overall minimum equals to the minimum of minimums, and 5) overall maximum equals to maximum of maximum. In this analysis, to avoid non-integer "Number of Positive Foods" when computing frequency distribution and histogram, the authors pretended that the 1000 repetitions of the same original dataset were actually 999 sets of new subjects of the same size added to the original sample. Once the summarization of data is done, frequency distributions and histrograms were generated for both "Number of Positive Foods ($90^{th}$)" and "Number of Positive Foods ($95^{th}$)" for both genders and for both IBS subjects and control subjects using programs "a_pos_foods.sas, a_pos_foods_by_dx.sas".

Method for Measuring Diagnostic Performance:

To measure diagnostic performance for each food items for each subject, we used data of "Number of Positive Foods ($90^{th}$)" and "Number of Positive Foods ($95^{th}$)" for each subject within each bootstrap replicate described above. In this analysis, the cutpoint was set to 1. Thus, if a subject has one or more "Number of Positive Foods ($90^{th}$)", then the subject is called "Has IBS." If a subject has less than one "Number of Positive Foods ($90^{th}$)", then the subject is called "Does Not Have IBS." When all calls were made, the calls were compared with actual diagnosis to determine whether a call was a True Positive (TP), True Negative (TN), False Positive (FP), or False Negative (FN). The comparisons were summarized across subjects to get the performance metrics of sensitivity, specificity, positive predictive value, and negative predictive value for both "Number of Positive Foods ($90^{th}$)" and "Number of Positive Foods ($95^{th}$)" when the cutpoint is set to 1 for each method. Each (sensitivity, 1-specificity) pair becomes a point on the ROC curve for this replicate.

To increase the accuracy, the analysis above was repeated by incrementing cutpoint from 2 up to 24, and repeated for each of the 1000 bootstrap replicates. Then the performance metrics across the 1000 bootstrap replicates were summarized by calculating averages using a program "t_pos_foods_ by_dx.sas". The results of diagnostic performance for female and male are shown in Table 13 (female) and Table 14 (male).

Of course, it should be appreciated that certain variations in the food preparations may be made without altering the inventive subject matter presented herein. For example, where the food item was yellow onion, that item should be understood to also include other onion varieties that were demonstrated to have equivalent activity in the tests. Indeed, the inventors have noted that for each tested food preparation, certain other related food preparations also tested in the same or equivalent manner (data not shown). Thus, it should be appreciated that each tested and claimed food preparation will have equivalent related preparations with demonstrated equal or equivalent reactions in the test.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

TABLE 1

| | | | |
|---|---|---|---|
| Abalone | Cured Cheese | Onion | Walnut, black |
| Adlay | Cuttlefish | Orange | Watermelon |
| Almond | Duck | Oyster | Welch Onion |
| American Cheese | Durian | Papaya | Wheat |
| Apple | Eel | Paprika | Wheat bran |
| Artichoke | Egg White (separate) | Parsley | Yeast (*S. cerevisiae*) |
| Asparagus | Egg Yolk (separate) | Peach | Yogurt |
| Avocado | Egg, white/yolk (comb.) | Peanut | |
| Baby Bok Choy | Eggplant | Pear | FOOD ADDITIVES |
| Bamboo shoots | Garlic | Pepper, Black | Arabic Gum |
| Banana | Ginger | Pineapple | Carboxymethyl Cellulose |
| Barley, whole grain | Gluten-Gliadin | Pinto bean | Carrageneenan |
| Beef | Goat's milk | Plum | FD&C Blue #1 |
| Beets | Grape, white/concord | Pork | FD&C Red #3 |
| Beta-lactoglobulin | Grapefruit | Potato | FD&C Red #40 |
| Blueberry | Grass Carp | Rabbit | FD&C Yellow #5 |
| Broccoli | Green Onion | Rice | FD&C Yellow #6 |
| Buckwheat | Green pea | Roquefort cheese | Gelatin |
| Butter | Green pepper | Rye | Guar Gum |
| Cabbage | Guava | Saccharine | Maltodextrin |
| Cane sugar | Hair Tail | Safflower seed | Pectin |
| Cantaloupe | Hake | Salmon | Whey |
| Caraway | Halibut | Sardine | Xanthan Gum |
| Carrot | Hazelnut | Scallop | |
| Casein | Honey | Sesame | |
| Cashew | Kelp | Shark fin | |
| Cauliflower | Kidney bean | Sheep's milk | |
| Celery | Kiwi Fruit | Shrimp | |
| Chard | Lamb | Sole | |
| Cheddar Cheese | Leek | Soybean | |
| Chick Peas | Lemon | Spinach | |
| Chicken | Lentils | Squashes | |
| Chili pepper | Lettuce, Iceberg | Squid | |
| Chocolate | Lima bean | Strawberry | |
| Cinnamon | Lobster | String bean | |
| Clam | Long.an | Sunflower seed | |
| Cocoa Bean | Mackerel | Sweet potato | |
| Coconut | Malt | Swiss cheese | |
| Codfish | Mango | Taro | |
| Coffee | Marjoram | Tea, black | |
| Cola nut | Millet | Tobacco | |
| Corn | Mung bean | Tomato | |

TABLE 1-continued

| | | |
|---|---|---|
| Cottage cheese | Mushroom | Trout |
| Cow's milk | Mustard seed | Tuna |
| Crab | Oat | Turkey |
| Cucumber | Olive | Vanilla |

Ranking of Foods According to 2-Tailed Permutation T-Test p-Values with FDR Adjustment

TABLE 2

| Rank | Food | Raw p-value | FDR Multiplicity-adj p-value |
|---|---|---|---|
| 1 | Cocoa | 0.0000 | 0.0000 |
| 2 | Black Tea | 0.0001 | 0.0020 |
| 3 | Oat | 0.0002 | 0.0032 |
| 4 | Cabbage | 0.0004 | 0.0032 |
| 5 | Cows Milk | 0.0004 | 0.0032 |
| 6 | Yellow Onion | 0.0006 | 0.0041 |
| 7 | Honey | 0.0008 | 0.0044 |
| 8 | Rye | 0.0010 | 0.0044 |
| 9 | Corn | 0.0010 | 0.0044 |
| 10 | Yeast | 0.0012 | 0.0047 |
| 11 | White Wheat | 0.0015 | 0.0055 |
| 12 | Soybean | 0.0020 | 0.0066 |
| 13 | Egg | 0.0022 | 0.0069 |
| 14 | Tuna | 0.0029 | 0.0084 |
| 15 | Lemon | 0.0036 | 0.0096 |
| 16 | Pineapple | 0.0045 | 0.0103 |
| 17 | Cucumber | 0.0046 | 0.0103 |
| 18 | Orange | 0.0046 | 0.0103 |
| 19 | Halibut | 0.0057 | 0.0120 |
| 20 | Walnut | 0.0062 | 0.0125 |
| 21 | Grapefruit | 0.0085 | 0.0161 |
| 22 | Cane Sugar | 0.0174 | 0.0316 |
| 23 | Chicken | 0.0184 | 0.0321 |
| 24 | Blueberry | 0.0218 | 0.0363 |
| 25 | US Gulf White Shrimp | 0.0230 | 0.0367 |
| 26 | Dungeness Crab | 0.0346 | 0.0533 |
| 27 | Barley | 0.0440 | 0.0652 |
| 28 | Strawberry | 0.0555 | 0.0793 |
| 29 | Pork | 0.0976 | 0.1312 |
| 30 | Brown Rice | 0.0984 | 0.1312 |
| 31 | Beef | 0.1067 | 0.1377 |
| 32 | Cashew | 0.1375 | 0.1718 |
| 33 | Codfish | 0.1741 | 0.2111 |
| 34 | Potato | 0.2443 | 0.2825 |
| 35 | White Sesame | 0.2472 | 0.2825 |
| 36 | Broccoli | 0.2589 | 0.2876 |
| 37 | Almond | 0.3174 | 0.3432 |
| 38 | Turkey | 0.4028 | 0.4240 |
| 39 | Scallop | 0.7149 | 0.7332 |
| 40 | Salmon | 0.9352 | 0.9352 |

Basic Descriptive Statistics of ELISA Score by Food and Gender Comparing IBS to Control

TABLE 3

| Sex | Food | Diagnosis | N | Mean | SD | Min | Max |
|---|---|---|---|---|---|---|---|
| F | Almond | Control | 26 | 0.227 | 0.124 | 0.100 | 0.565 |
| | | IBS | 46 | 0.358 | 0.474 | 0.078 | 3.065 |
| | | Diff (1–2) | — | −0.132 | 0.387 | — | — |
| | Barley | Control | 26 | 0.255 | 0.144 | 0.093 | 0.725 |
| | | IBS | 46 | 0.450 | 0.361 | 0.118 | 1.676 |
| | | Diff (1–2) | — | −0.195 | 0.302 | — | — |
| | Beef | Control | 26 | 0.170 | 0.081 | 0.086 | 0.439 |
| | | IBS | 45 | 0.190 | 0.090 | 0.072 | 0.467 |
| | | Diff (1–2) | — | −0.020 | 0.087 | — | — |
| | Black Tea | Control | 26 | 0.179 | 0.075 | 0.069 | 0.307 |
| | | IBS | 46 | 0.272 | 0.086 | 0.115 | 0.508 |
| | | Diff (1–2) | — | −0.093 | 0.083 | — | — |
| | Blueberry | Control | 26 | 0.425 | 0.190 | 0.233 | 1.061 |
| | | IBS | 46 | 0.480 | 0.143 | 0.239 | 0.867 |
| | | Diff (1–2) | — | −0.055 | 0.162 | — | — |
| | Broccoli | Control | 26 | 0.220 | 0.127 | 0.118 | 0.620 |
| | | IBS | 46 | 0.280 | 0.174 | 0.106 | 1.042 |
| | | Diff (1–2) | — | −0.059 | 0.159 | — | — |
| | Brown Rice | Control | 26 | 0.236 | 0.118 | 0.082 | 0.449 |
| | | IBS | 46 | 0.253 | 0.136 | 0.101 | 0.690 |
| | | Diff (1–2) | — | −0.018 | 0.130 | — | — |
| | Cabbage | Control | 26 | 0.285 | 0.161 | 0.086 | 0.642 |
| | | IBS | 46 | 0.432 | 0.173 | 0.132 | 1.033 |
| | | Diff (1–2) | — | −0.147 | 0.169 | — | — |
| | Cane Sugar | Control | 26 | 0.377 | 0.272 | 0.070 | 0.835 |
| | | IBS | 46 | 0.521 | 0.234 | 0.107 | 0.975 |
| | | Diff (1–2) | — | −0.143 | 0.248 | — | — |
| | Cashew | Control | 26 | 0.249 | 0.277 | 0.080 | 1.528 |
| | | IBS | 46 | 0.286 | 0.215 | 0.081 | 1.183 |
| | | Diff (1–2) | — | −0.037 | 0.239 | — | — |
| | Chicken | Control | 25 | 0.123 | 0.064 | 0.056 | 0.314 |
| | | IBS | 46 | 0.156 | 0.097 | 0.062 | 0.579 |
| | | Diff (1–2) | — | −0.033 | 0.087 | — | — |
| | Cocoa | Control | 26 | 0.345 | 0.151 | 0.142 | 0.656 |
| | | IBS | 46 | 0.587 | 0.349 | 0.208 | 2.030 |
| | | Diff (1–2) | — | −0.242 | 0.294 | — | — |
| | Codfish | Control | 26 | 0.202 | 0.081 | 0.083 | 0.392 |
| | | IBS | 46 | 0.182 | 0.180 | 0.048 | 1.069 |
| | | Diff (1–2) | — | 0.020 | 0.152 | — | — |
| | Corn | Control | 26 | 0.416 | 0.221 | 0.114 | 0.923 |
| | | IBS | 47 | 0.562 | 0.333 | 0.146 | 1.686 |
| | | Diff (1–2) | — | −0.146 | 0.298 | — | — |
| | Cow Milk | Control | 26 | 0.676 | 0.538 | 0.074 | 2.212 |
| | | IBS | 46 | 1.191 | 0.845 | 0.134 | 3.035 |
| | | Diff (1–2) | — | −0.515 | 0.750 | — | — |
| | Cucumber | Control | 26 | 0.168 | 0.083 | 0.079 | 0.317 |
| | | IBS | 46 | 0.211 | 0.071 | 0.088 | 0.460 |
| | | Diff (1–2) | — | −0.043 | 0.075 | — | — |
| | Dungeness Crab | Control | 26 | 0.321 | 0.187 | 0.107 | 0.757 |
| | | IBS | 46 | 0.390 | 0.226 | 0.082 | 1.285 |
| | | Diff (1–2) | — | −0.068 | 0.213 | — | — |
| | Egg | Control | 26 | 0.336 | 0.296 | 0.060 | 1.119 |
| | | IBS | 46 | 0.903 | 0.858 | 0.115 | 3.274 |
| | | Diff (1–2) | — | −0.567 | 0.710 | — | — |
| | Grapefruit | Control | 25 | 0.154 | 0.088 | 0.069 | 0.458 |
| | | IBS | 46 | 0.203 | 0.148 | 0.085 | 1.014 |
| | | Diff (1–2) | — | −0.049 | 0.130 | — | — |
| | Halibut | Control | 26 | 0.246 | 0.125 | 0.093 | 0.544 |
| | | IBS | 46 | 0.348 | 0.198 | 0.103 | 0.941 |
| | | Diff (1–2) | — | −0.101 | 0.175 | — | — |
| | Honey | Control | 26 | 0.584 | 0.306 | 0.152 | 1.463 |
| | | IBS | 46 | 0.805 | 0.364 | 0.200 | 1.638 |
| | | Diff (1–2) | — | −0.220 | 0.344 | — | — |
| | Lemon | Control | 26 | 0.282 | 0.157 | 0.080 | 0.635 |
| | | IBS | 45 | 0.444 | 0.297 | 0.120 | 1.567 |
| | | Diff (1–2) | — | −0.162 | 0.255 | — | — |
| | Oat | Control | 26 | 0.282 | 0.253 | 0.071 | 1.116 |
| | | IBS | 47 | 0.693 | 0.680 | 0.086 | 2.934 |
| | | Diff (1–2) | — | −0.411 | 0.567 | — | — |
| | Orange | Control | 26 | 0.222 | 0.119 | 0.080 | 0.549 |
| | | IBS | 46 | 0.313 | 0.166 | 0.106 | 1.044 |
| | | Diff (1–2) | — | −0.091 | 0.151 | — | — |

TABLE 3-continued

| Sex | Food | Diagnosis | N | ELISA Score Mean | SD | Min | Max |
|---|---|---|---|---|---|---|---|
|  | Pineapple | Control | 26 | 0.924 | 0.853 | 0.098 | 3.467 |
|  |  | IBS | 47 | 1.624 | 1.015 | 0.206 | 3.721 |
|  |  | Diff (1–2) | — | −0.700 | 0.961 | — | — |
|  | Pork | Control | 26 | 0.392 | 0.266 | 0.107 | 1.285 |
|  |  | IBS | 46 | 0.466 | 0.283 | 0.064 | 1.248 |
|  |  | Diff (1–2) | — | −0.074 | 0.277 | — | — |
|  | Potato | Control | 26 | 0.209 | 0.104 | 0.075 | 0.441 |
|  |  | IBS | 46 | 0.266 | 0.089 | 0.087 | 0.474 |
|  |  | Diff (1–2) | — | −0.057 | 0.095 | — | — |
|  | Rye | Control | 26 | 0.138 | 0.054 | 0.073 | 0.299 |
|  |  | IBS | 47 | 0.249 | 0.193 | 0.080 | 1.248 |
|  |  | Diff (1–2) | — | −0.111 | 0.159 | — | — |
|  | Salmon | Control | 26 | 0.230 | 0.140 | 0.102 | 0.684 |
|  |  | IBS | 46 | 0.196 | 0.100 | 0.058 | 0.444 |
|  |  | Diff (1–2) | — | 0.034 | 0.116 | — | — |
|  | Scallop | Control | 25 | 0.283 | 0.205 | 0.086 | 1.025 |
|  |  | IBS | 46 | 0.277 | 0.173 | 0.102 | 0.860 |
|  |  | Diff (1–2) | — | 0.005 | 0.185 | — | — |
|  | Soybean | Control | 26 | 0.508 | 0.228 | 0.210 | 0.849 |
|  |  | IBS | 46 | 0.658 | 0.230 | 0.252 | 1.101 |
|  |  | Diff (1–2) | — | −0.150 | 0.229 | — | — |
|  | Strawberry | Control | 26 | 0.145 | 0.059 | 0.060 | 0.259 |
|  |  | IBS | 46 | 0.176 | 0.056 | 0.075 | 0.370 |
|  |  | Diff (1–2) | — | −0.031 | 0.057 | — | — |
|  | Tuna | Control | 26 | 0.588 | 0.297 | 0.202 | 1.375 |
|  |  | IBS | 46 | 0.859 | 0.431 | 0.181 | 1.875 |
|  |  | Diff (1–2) | — | −0.271 | 0.388 | — | — |
|  | Turkey | Control | 26 | 0.248 | 0.110 | 0.072 | 0.583 |
|  |  | IBS | 46 | 0.267 | 0.110 | 0.112 | 0.691 |
|  |  | Diff (1–2) | — | −0.019 | 0.110 | — | — |
|  | US Gulf White Shrimp | Control | 26 | 0.563 | 0.325 | 0.188 | 1.693 |
|  |  | IBS | 45 | 0.834 | 0.459 | 0.210 | 2.135 |
|  |  | Diff (1–2) | — | −0.271 | 0.415 | — | — |
|  | Walnut | Control | 26 | 0.194 | 0.070 | 0.096 | 0.315 |
|  |  | IBS | 46 | 0.273 | 0.123 | 0.135 | 0.944 |
|  |  | Diff (1–2) | — | −0.079 | 0.107 | — | — |
|  | White Sesame | Control | 26 | 0.705 | 0.524 | 0.190 | 2.663 |
|  |  | IBS | 46 | 0.734 | 0.393 | 0.126 | 1.967 |
|  |  | Diff (1–2) | — | −0.029 | 0.444 | — | — |
|  | White Wheat | Control | 26 | 0.228 | 0.125 | 0.106 | 0.576 |
|  |  | IBS | 47 | 0.427 | 0.355 | 0.096 | 1.872 |
|  |  | Diff (1–2) | — | −0.198 | 0.295 | — | — |
|  | Yeast | Control | 25 | 0.963 | 0.624 | 0.157 | 2.364 |
|  |  | IBS | 46 | 1.291 | 0.844 | 0.247 | 3.438 |
|  |  | Diff (1–2) | — | −0.327 | 0.775 | — | — |
|  | Yellow Onion | Control | 26 | 0.570 | 0.442 | 0.105 | 1.497 |
|  |  | IBS | 46 | 0.911 | 0.439 | 0.129 | 1.791 |
|  |  | Diff (1–2) | — | −0.341 | 0.440 | — | — |
| M | Almond | Control | 89 | 0.335 | 0.391 | 0.077 | 2.342 |
|  |  | IBS | 29 | 0.361 | 0.341 | 0.069 | 1.442 |
|  |  | Diff (1–2) | — | −0.026 | 0.379 | — | — |
|  | Barley | Control | 89 | 0.419 | 0.430 | 0.110 | 2.242 |
|  |  | IBS | 29 | 0.525 | 0.499 | 0.092 | 1.935 |
|  |  | Diff (1–2) | — | −0.106 | 0.448 | — | — |
|  | Beef | Control | 73 | 0.184 | 0.127 | 0.081 | 0.979 |
|  |  | IBS | 27 | 0.222 | 0.102 | 0.078 | 0.555 |
|  |  | Diff (1–2) | — | −0.038 | 0.121 | — | — |
|  | Black Tea | Control | 89 | 0.209 | 0.088 | 0.080 | 0.522 |
|  |  | IBS | 29 | 0.242 | 0.076 | 0.118 | 0.395 |
|  |  | Diff (1–2) | — | −0.033 | 0.086 | — | — |
|  | Blueberry | Control | 89 | 0.425 | 0.228 | 0.216 | 2.031 |
|  |  | IBS | 29 | 0.517 | 0.207 | 0.278 | 1.424 |
|  |  | Diff (1–2) | — | −0.092 | 0.223 | — | — |
|  | Broccoli | Control | 89 | 0.242 | 0.204 | 0.096 | 1.747 |
|  |  | IBS | 29 | 0.263 | 0.194 | 0.133 | 1.116 |
|  |  | Diff (1–2) | — | −0.021 | 0.201 | — | — |
|  | Brown Rice | Control | 89 | 0.237 | 0.123 | 0.081 | 0.714 |
|  |  | IBS | 29 | 0.288 | 0.122 | 0.090 | 0.554 |
|  |  | Diff (1–2) | — | −0.051 | 0.122 | — | — |
|  | Cabbage | Control | 89 | 0.322 | 0.173 | 0.089 | 0.873 |
|  |  | IBS | 29 | 0.409 | 0.192 | 0.105 | 0.878 |
|  |  | Diff (1–2) | — | −0.087 | 0.178 | — | — |
|  | Cane Sugar | Control | 89 | 0.375 | 0.255 | 0.076 | 1.097 |
|  |  | IBS | 29 | 0.446 | 0.230 | 0.098 | 0.804 |
|  |  | Diff (1–2) | — | −0.071 | 0.249 | — | — |
|  | Cashew | Control | 89 | 0.230 | 0.157 | 0.078 | 1.152 |
|  |  | IBS | 29 | 0.291 | 0.167 | 0.072 | 0.686 |
|  |  | Diff (1–2) | — | −0.062 | 0.160 | — | — |
|  | Chicken | Control | 88 | 0.134 | 0.069 | 0.055 | 0.339 |
|  |  | IBS | 29 | 0.172 | 0.087 | 0.055 | 0.385 |
|  |  | Diff (1–2) | — | −0.037 | 0.074 |  |  |
|  | Cocoa | Control | 89 | 0.399 | 0.198 | 0.158 | 1.386 |
|  |  | IBS | 29 | 0.623 | 0.294 | 0.209 | 1.310 |
|  |  | Diff (1–2) | — | −0.224 | 0.225 | — | — |
|  | Codfish | Control | 89 | 0.198 | 0.191 | 0.072 | 1.759 |
|  |  | IBS | 29 | 0.146 | 0.053 | 0.071 | 0.325 |
|  |  | Diff (1–2) | — | 0.053 | 0.169 | — | — |
|  | Corn | Control | 89 | 0.414 | 0.240 | 0.137 | 1.185 |
|  |  | IBS | 29 | 0.618 | 0.330 | 0.183 | 1.310 |
|  |  | Diff (1–2) | — | −0.204 | 0.265 | — | — |
|  | Cow Milk | Control | 89 | 0.805 | 0.621 | 0.095 | 2.416 |
|  |  | IBS | 29 | 1.309 | 0.946 | 0.128 | 3.525 |
|  |  | Diff (1–2) | — | −0.504 | 0.713 | — | — |
|  | Cucumber | Control | 89 | 0.167 | 0.069 | 0.070 | 0.343 |
|  |  | IBS | 29 | 0.197 | 0.070 | 0.079 | 0.322 |
|  |  | Diff (1–2) | — | −0.030 | 0.069 | — | — |
|  | Dungeness Crab | Control | 89 | 0.342 | 0.175 | 0.104 | 1.047 |
|  |  | IBS | 29 | 0.431 | 0.249 | 0.082 | 0.992 |
|  |  | Diff (1–2) | — | −0.089 | 0.195 | — | — |
|  | Egg | Control | 89 | 0.407 | 0.385 | 0.071 | 1.799 |
|  |  | IBS | 29 | 0.609 | 0.681 | 0.094 | 2.589 |
|  |  | Diff (1–2) | — | −0.202 | 0.474 | — | — |
|  | Grapefruit | Control | 88 | 0.182 | 0.100 | 0.063 | 0.613 |
|  |  | IBS | 29 | 0.260 | 0.185 | 0.058 | 0.658 |
|  |  | Diff (1–2) | — | −0.079 | 0.126 | — | — |
|  | Halibut | Control | 89 | 0.284 | 0.153 | 0.105 | 0.751 |
|  |  | IBS | 29 | 0.379 | 0.267 | 0.112 | 1.477 |
|  |  | Diff (1–2) | — | −0.095 | 0.187 | — | — |
|  | Honey | Control | 89 | 0.644 | 0.358 | 0.210 | 2.059 |
|  |  | IBS | 29 | 0.911 | 0.557 | 0.227 | 2.635 |
|  |  | Diff (1–2) | — | −0.267 | 0.415 | — | — |
|  | Lemon | Control | 89 | 0.358 | 0.239 | 0.091 | 1.254 |
|  |  | IBS | 29 | 0.503 | 0.375 | 0.082 | 1.709 |
|  |  | Diff (1–2) | — | −0.146 | 0.278 | — | — |
|  | Oat | Control | 89 | 0.384 | 0.378 | 0.066 | 1.972 |
|  |  | IBS | 29 | 0.745 | 0.666 | 0.101 | 2.614 |
|  |  | Diff (1–2) | — | −0.361 | 0.464 |  |  |
|  | Orange | Control | 89 | 0.265 | 0.152 | 0.079 | 0.831 |
|  |  | IBS | 29 | 0.358 | 0.252 | 0.076 | 1.126 |
|  |  | Diff (1–2) | — | −0.093 | 0.181 | — | — |
|  | Pineapple | Control | 89 | 1.053 | 0.915 | 0.123 | 3.617 |
|  |  | IBS | 29 | 1.354 | 0.883 | 0.287 | 3.126 |
|  |  | Diff (1–2) | — | −0.301 | 0.908 | — | — |
|  | Pork | Control | 89 | 0.388 | 0.219 | 0.110 | 1.216 |
|  |  | IBS | 29 | 0.462 | 0.244 | 0.126 | 1.057 |
|  |  | Diff (1–2) | — | −0.075 | 0.225 | — | — |
|  | Potato | Control | 89 | 0.249 | 0.170 | 0.069 | 1.408 |
|  |  | IBS | 29 | 0.253 | 0.125 | 0.100 | 0.578 |
|  |  | Diff (1–2) | — | −0.004 | 0.161 | — | — |
|  | Rye | Control | 89 | 0.178 | 0.100 | 0.079 | 0.610 |
|  |  | IBS | 29 | 0.237 | 0.129 | 0.088 | 0.651 |
|  |  | Diff (1–2) | — | −0.060 | 0.108 | — | — |
|  | Salmon | Control | 89 | 0.206 | 0.132 | 0.073 | 0.897 |
|  |  | IBS | 29 | 0.229 | 0.185 | 0.114 | 1.065 |
|  |  | Diff (1–2) | — | −0.022 | 0.147 | — | — |
|  | Scallop | Control | 88 | 0.294 | 0.187 | 0.095 | 0.973 |
|  |  | IBS | 29 | 0.320 | 0.222 | 0.067 | 1.161 |
|  |  | Diff (1–2) | — | −0.026 | 0.196 | — | — |
|  | Soybean | Control | 89 | 0.523 | 0.292 | 0.175 | 1.653 |
|  |  | IBS | 29 | 0.715 | 0.490 | 0.187 | 2.583 |
|  |  | Diff (1–2) | — | −0.191 | 0.351 | — | — |
|  | Strawberry | Control | 89 | 0.151 | 0.058 | 0.062 | 0.311 |
|  |  | IBS | 29 | 0.161 | 0.053 | 0.077 | 0.252 |
|  |  | Diff (1–2) | — | −0.010 | 0.057 | — | — |
|  | Tuna | Control | 89 | 0.725 | 0.369 | 0.183 | 1.752 |
|  |  | IBS | 29 | 0.899 | 0.459 | 0.213 | 1.952 |
|  |  | Diff (1–2) | — | −0.174 | 0.393 | — | — |
|  | Turkey | Control | 89 | 0.252 | 0.109 | 0.100 | 0.711 |
|  |  | IBS | 29 | 0.265 | 0.099 | 0.109 | 0.510 |
|  |  | Diff (1–2) | — | −0.013 | 0.107 | — | — |

TABLE 3-continued

| Sex | Food | Diagnosis | N | ELISA Score Mean | SD | Min | Max |
|---|---|---|---|---|---|---|---|
| | US Gulf White Shrimp | Control | 89 | 0.709 | 0.366 | 0.226 | 1.982 |
| | | IBS | 29 | 0.797 | 0.422 | 0.222 | 1.550 |
| | | Diff (1–2) | — | −0.089 | 0.380 | — | — |
| | Walnut | Control | 89 | 0.216 | 0.110 | 0.095 | 0.839 |
| | | IBS | 29 | 0.244 | 0.085 | 0.101 | 0.428 |
| | | Diff (1–2) | — | −0.029 | 0.104 | — | — |
| | White Sesame | Control | 89 | 0.620 | 0.375 | 0.112 | 1.855 |
| | | IBS | 29 | 0.744 | 0.412 | 0.153 | 1.970 |
| | | Diff (1–2) | — | −0.124 | 0.385 | — | — |
| | White Wheat | Control | 89 | 0.290 | 0.250 | 0.095 | 1.681 |
| | | IBS | 29 | 0.463 | 0.400 | 0.130 | 1.561 |
| | | Diff (1–2) | — | −0.173 | 0.293 | — | — |
| | Yeast | Control | 88 | 0.940 | 0.624 | 0.172 | 3.157 |
| | | IBS | 29 | 1.481 | 0.788 | 0.416 | 2.892 |
| | | Diff (1–2) | — | −0.541 | 0.668 | — | — |
| | Yellow Onion | Control | 89 | 0.558 | 0.418 | 0.094 | 1.672 |
| | | IBS | 29 | 0.760 | 0.417 | 0.098 | 1.507 |
| | | Diff (1–2) | — | −0.203 | 0.418 | — | — |

Upper Quantiles of ELISA Signal Scores Among Control Subjects as Candidates for Test Cutpoints in Determining "Positive" or "Negative"

Top 24 Foods Ranked by Descending Order of Discriminatory Ability Using Permutation Test

TABLE 4

| Food Ranking | Food | Sex | Cutpoint 90th percentile | 95th percentile |
|---|---|---|---|---|
| 1 | Cocoa | F | 0.544 | 0.587 |
| | | M | 0.581 | 0.721 |
| 2 | BlackTea | F | 0.281 | 0.296 |
| | | M | 0.337 | 0.379 |
| 3 | Oat | F | 0.647 | 0.813 |
| | | M | 0.880 | 1.187 |
| 4 | Cabbage | F | 0.507 | 0.573 |
| | | M | 0.542 | 0.644 |
| 5 | CowsMilk | F | 1.373 | 1.611 |
| | | M | 1.872 | 2.133 |
| 6 | YellowOnion | F | 1.109 | 1.214 |
| | | M | 1.142 | 1.328 |
| 7 | Honey | F | 1.022 | 1.189 |
| | | M | 1.111 | 1.422 |
| 8 | Rye | F | 0.209 | 0.237 |
| | | M | 0.313 | 0.400 |
| 9 | Corn | F | 0.755 | 0.835 |
| | | M | 0.774 | 0.904 |
| 10 | Yeast | F | 1.811 | 2.014 |
| | | M | 1.883 | 2.102 |
| 11 | WhiteWheat | F | 0.409 | 0.477 |
| | | M | 0.492 | 0.704 |
| 12 | Soybean | F | 0.778 | 0.806 |
| | | M | 0.891 | 1.076 |
| 13 | Egg | F | 0.794 | 0.932 |
| | | M | 0.988 | 1.270 |
| 14 | Tuna | F | 1.054 | 1.208 |
| | | M | 1.276 | 1.472 |
| 15 | Lemon | F | 0.533 | 0.585 |
| | | M | 0.705 | 0.885 |
| 16 | Pineapple | F | 2.139 | 2.646 |
| | | M | 2.651 | 3.030 |
| 17 | Cucumber | F | 0.289 | 0.305 |
| | | M | 0.265 | 0.301 |
| 18 | Orange | F | 0.389 | 0.456 |
| | | M | 0.483 | 0.589 |
| 19 | Halibut | F | 0.451 | 0.497 |
| | | M | 0.506 | 0.600 |

TABLE 4-continued

| Food Ranking | Food | Sex | Cutpoint 90th percentile | 95th percentile |
|---|---|---|---|---|
| 20 | Walnut | F | 0.288 | 0.297 |
| | | M | 0.319 | 0.387 |
| 21 | Grapefruit | F | 0.267 | 0.333 |
| | | M | 0.328 | 0.380 |
| 22 | CaneSugar | F | 0.739 | 0.775 |
| | | M | 0.746 | 0.834 |
| 23 | Chicken | F | 0.214 | 0.249 |
| | | M | 0.250 | 0.275 |
| 24 | Blueberry | F | 0.676 | 0.807 |
| | | M | 0.630 | 0.787 |

TABLE 5

| IBS Population | | Non-IBS Population | |
|---|---|---|---|
| Sample ID | # of Positive Results based on 90th Percentile | Sample ID | # of Positive Results based on 90th |
| IBS-3 | 5 | BRH-768035 | 0 |
| IBS-5 | 0 | BRH-768034 | 1 |
| IBS-11 | 1 | BRH-768033 | 1 |
| IBS-12 | 9 | BRH-768032 | 1 |
| IBS-14 | 0 | BRH-768031 | 1 |
| IBS-18 | 0 | BRH-763484 | 0 |
| IBS-19 | 1 | BRH-768029 | 10 |
| IBS-23 | 11 | BRH-768028 | 8 |
| IBS-24 | 1 | BRH-763510 | 4 |
| IBS-30 | 9 | BRH-768036 | 0 |
| IBS-33 | 8 | BRH-768037 | 1 |
| IBS-35 | 7 | BRH-768038 | 1 |
| IBS-38 | 6 | BRH-768039 | 0 |
| IBS-40 | 3 | BRH-768040 | 0 |
| IBS-42 | 6 | BRH-768041 | 1 |
| IBS-43 | 2 | BRH-768042 | 1 |
| BRH-698596 | 4 | BRH-768043 | 5 |
| BHR-698597 | 9 | BRH-768044 | 3 |
| BRH-698598 | 4 | BRH-768055 | 1 |
| BRH-698599 | 18 | BRH-768054 | 1 |
| BRH-698600 | 3 | BRH-764371 | 0 |
| BRH-698621 | 12 | BRH-768056 | 2 |
| BRH-698622 | 7 | BRH-764372 | 2 |
| BRH-698623 | 5 | BRH-764377 | 5 |
| BRH-698624 | 1 | BRH-764378 | 2 |
| BRH-698625 | 9 | BRH-763531 | 1 |
| BRH-774496 | 17 | BRH-764329 | 0 |
| BRH-763476 | 0 | BRH-763533 | 0 |
| BRH-768030 | 0 | BRH-763529 | 0 |
| IBS-2 | 1 | BRH-763553 | 12 |
| IBS-4 | 1 | BRH-763528 | 0 |
| IBS-6 | 1 | BRH-763509 | 0 |
| IBS-7 | 9 | BRH-763517 | 2 |
| IBS-8 | 9 | BRH-763500 | 0 |
| IBS-9 | 1 | BRH-764332 | 0 |
| IBS-10 | 14 | BRH-764338 | 1 |
| IBS-13 | 19 | BRH-764337 | 3 |
| IBS-15 | 9 | BRH-764341 | 1 |
| IBS-16 | 1 | BRH-764340 | 1 |
| IBS-17 | 9 | BRH-764342 | 0 |
| IBS-20 | 16 | BRH-764347 | 1 |
| IBS-21 | 23 | BRH-764343 | 5 |
| IBS-22 | 20 | BRH-774498 | 1 |
| IBS-25 | 2 | BRH-768027 | 12 |
| IBS-26 | 16 | BRH-768000 | 1 |
| IBS-27 | 8 | BRH-774499 | 12 |
| IBS-28 | 10 | BRH-774502 | 4 |
| IBS-29 | 8 | BRH-774504 | 8 |
| IBS-31 | 4 | BRH-767999 | 0 |
| IBS-32 | 2 | BRH-764350 | 0 |

TABLE 5-continued

| IBS Population | | Non-IBS Population | |
|---|---|---|---|
| Sample ID | # of Positive Results based on 90th Percentile | Sample ID | # of Positive Results based on 90th |
| IBS-34 | 0 | BRH-763534 | 0 |
| IBS-36 | 3 | BRH-763506 | 0 |
| IBS-37 | 5 | BRH-774495 | 2 |
| IBS-39 | 19 | BRH-764353 | 0 |
| IBS-41 | 5 | BRH-764355 | 0 |
| IBS-44 | 5 | BRH-764356 | 0 |
| BRH-698601 | 10 | BRH-764361 | 1 |
| BRH-698602 | 3 | BRH-764368 | 1 |
| BRH-698603 | 13 | BRH-768053 | 2 |
| BRH-698604 | 10 | BRH-764370 | 1 |
| BRH-698605 | 8 | BRH-764346 | 0 |
| BRH-698606 | 4 | BRH-768052 | 0 |
| BRH-698607 | 2 | BRH-764335 | 10 |
| BRH-698608 | 4 | BRH-774510 | 2 |
| BRH-698609 | 1 | BRH-774511 | 0 |
| BRH-698610 | 1 | BRH-768001 | 2 |
| BRH-698611 | 3 | BRH-768007 | 0 |
| BRH-698612 | 3 | BRH-768008 | 3 |
| BRH-698613 | 12 | BRH-767995 | 0 |
| BRH-698614 | 11 | BRH-767992 | 3 |
| BRH-698615 | 4 | BRH-767991 | 0 |
| BRH-698616 | 5 | BRH-764344 | 2 |
| BRH-698617 | 11 | BRH-764386 | 0 |
| BRH-698618 | 6 | BRH-763513 | 7 |
| BRH-698619 | 9 | BRH-763530 | 5 |
| BRH-698620 | 6 | BRH-764345 | 1 |
| No of observation | 76 | BRH-764336 | 0 |
| Average # of | 6.63 | BRH-764352 | 4 |
| SD | 5.54 | BRH-764360 | 0 |
| | | BRH-764339 | 4 |
| | | BRH-763527 | 17 |
| | | BRH-764334 | 1 |
| | | BRH-764349 | 0 |
| | | BRH-764380 | 0 |
| | | BRH-764366 | 0 |
| | | BRH-763526 | 19 |
| | | BRH-764351 | 2 |
| | | BRH-763503 | 3 |
| | | BRH-764365 | 3 |
| | | BRH-764381 | 0 |
| | | BRH-763523 | 0 |
| | | BRH-774500 | 3 |
| | | BRH-774501 | 1 |
| | | BRH-774505 | 6 |
| | | BRH-774503 | 2 |
| | | BRH-774494 | 0 |
| | | BRH-774493 | 0 |
| | | BRH-774492 | 1 |
| | | BRH-774491 | 0 |
| | | BRH-764357 | 2 |
| | | BRH-764358 | 0 |
| | | BRH-768045 | 0 |
| | | BRH-768047 | 1 |
| | | BRH-768048 | 8 |
| | | BRH-768049 | 12 |
| | | BRH-768051 | 0 |
| | | BRH-768050 | 5 |
| | | BRH-774506 | 11 |
| | | BRH-774507 | 0 |
| | | BRH-774509 | 0 |
| | | BRH-774512 | 0 |
| | | BRH-774513 | 4 |
| | | BRH-774514 | 1 |
| | | BRH-764359 | 3 |
| | | BRH-763524 | 1 |
| | | No of observation | 115 |
| | | Average # of | 2.37 |
| | | SD | 3.67 |

TABLE 6

| Variable | IBS IBS |
|---|---|
| Sample size | 76 |
| Lowest value | 0.0000 |
| Highest value | 23.0000 |
| Arithmetic mean | 6.6316 |
| 95% Cl for the mean | 5.3651 to 7.8980 |
| Median | 5.0000 |
| 95% Cl for the median | 4.0000 to 8.0000 |
| Variance | 30.7158 |
| Standard deviation | 5.5422 |
| Relative standard deviation | 0.8357 (83.57%) |
| Standard error of the mean | 0.6357 |
| Coefficient of Skewness | 0.9423 ($P = 0.0017$) |
| Coefficient of Kurtosis | 0.3684 ($P = 0.4053$) |
| D'Agostino-Pearson test for Normal distribution | reject Normality ($P = 0.0051$) |

| Percentiles | | 95% Confidence Interval |
|---|---|---|
| 2.5 | 0.0000 | |
| 5 | 0.0000 | 0.0000 to 1.0000 |
| 10 | 1.0000 | 0.0000 to 1.0000 |
| 25 | 2.0000 | 1.0000 to 3.1043 |
| 75 | 9.0000 | 8.8957 to 11.6255 |
| 90 | 15.8000 | 11.0000 to 19.0000 |
| 95 | 18.7000 | 15.2303 to 22.7004 |
| 97.5 | 19.6000 | |

TABLE 7

| Variable | Non_IBS Non-IBS |
|---|---|
| Sample size | 115 |
| Lowest value | 0.0000 |
| Highest value | 19.0000 |
| Arithmetic mean | 2.3652 |
| 95% Cl for the mean | 1.6879 to 3.0426 |
| Median | 1.0000 |
| 95% Cl for the median | 1.0000 to 1.0000 |
| Variance | 13.4444 |
| Standard deviation | 3.6667 |
| Relative standard deviation | 1.5502 (155.02%) |
| Standard error of the mean | 0.3419 |
| Coefficient of Skewness | 2.3537 ($P < 0.0001$) |
| Coefficient of Kurtosis | 5.8546 ($P < 0.0001$) |
| D'Agostino-Pearson test for Normal distribution | reject Normality ($P < 0.0001$) |

| Percentiles | | 95% Confidence Interval |
|---|---|---|
| 2.5 | 0.0000 | |
| 5 | 0.0000 | 0.0000 to 0.0000 |
| 10 | 0.0000 | 0.0000 to 0.0000 |
| 25 | 0.0000 | 0.0000 to 0.0000 |
| 75 | 3.0000 | 2.0000 to 4.0000 |
| 90 | 8.0000 | 5.0000 to 11.8759 |
| 95 | 11.7500 | 8.0000 to 16.1360 |
| 97.5 | 12.0000 | |

TABLE 8

| Variable | IBS_1 IBS |
|---|---|
| Back-transformed after logarithmic transformation. | |
| Sample size | 76 |
| Lowest value | 0.1000 |
| Highest value | 23.0000 |
| Geometric mean | 3.7394 |
| 95% Cl for the mean | 2.7247 to 5.1321 |
| Median | 5.0000 |

TABLE 8-continued

| | |
|---|---|
| 95% Cl for the median | 4.0000 to 8.0000 |
| Coefficient of Skewness | −1.3159 (P = 0.0001) |
| Coefficient of Kurtosis | 1.3551 (P = 0.0481) |
| D'Agostino-Pearson test for Normal distribution | reject Normality (P < 0.0001) |

| Percentiles | | 95% Confidence Interval |
|---|---|---|
| 2.5 | 0.1000 | |
| 5 | 0.1000 | 0.1000 to 1.0000 |
| 10 | 1.0000 | 0.1000 to 1.0000 |
| 25 | 2.0000 | 1.0000 to 3.0914 |
| 75 | 9.0000 | 8.8901 to 11.6153 |
| 90 | 15.7878 | 11.0000 to 19.0000 |
| 95 | 18.6943 | 15.1985 to 22.6812 |
| 97.5 | 19.5938 | |

TABLE 9

| Variable | non_IBS_1<br>non-IBS 1 |
|---|---|
| | Back-transformed after logarithmic transformation. |
| Sample size | 115 |
| Lowest value | 0.1000 |
| Highest value | 19.0000 |
| Geometric mean | 0.7278 |
| 95% Cl for the mean | 0.5297 to 1.0001 |
| Median | 1.0000 |
| 95% Cl for the median | 1.0000 to 1.0000 |
| Coefficient of Skewness | 0.04343 (P = 0.8428) |
| Coefficient of Kurtosis | −1.4006 (P < 0.0001) |
| D'Agostino-Pearson test for Normal distribution | reject Normality (P < 0.0001) |

| Percentiles | | 95% Confidence Interval |
|---|---|---|
| 2.5 | 0.1000 | |
| 5 | 0.1000 | 0.1000 to 0.1000 |
| 10 | 0.1000 | 0.1000 to 0.1000 |
| 25 | 0.1000 | 0.1000 to 0.1000 |
| 75 | 3.0000 | 2.0000 to 4.0000 |
| 90 | 8.0000 | 5.0000 to 11.8711 |
| 95 | 11.7418 | 8.0000 to 16.0070 |
| 97.5 | 12.0000 | |

TABLE 10

| Sample 1 | |
|---|---|
| Variable | IBS_1<br>IBS 1 |

TABLE 10-continued

| Sample 2 | | |
|---|---|---|
| Variable | | non_IBS_1<br>non-IBS 1 |
| Back-transformed after logarithmic transformation. | | |
| | Sample 1 | Sample 2 |
| Sample size | 76 | 115 |
| Geometric mean | 3.7394 | 0.7278 |
| 95% Cl for the mean | 2.7247 to 5.1321 | 0.5297 to 1.0001 |
| Variance of Logs | 0.3620 | 0.5582 |
| F-test for equal variances | P = 0.045 | |

| T-test (assuming equal variances)<br>Difference on Log-transformed scale | |
|---|---|
| Difference | −0.7108 |
| Standard Error | 0.1025 |
| 95% Cl of difference | −0.9129 to −0.5087 |
| Test statistic t | −6.937 |
| Degrees of Freedom (DF) | 189 |
| Two-tailed probability | P < 0.0001 |

| Back-transformed results | |
|---|---|
| Ratio of geometric means | 0.1946 |
| 95% Cl of ratio | 0.1222 to 0.3100 |

TABLE 11

| Sample 1 | | |
|---|---|---|
| Variable | | IBS_1<br>IBS-1 |
| Sample 2 | | |
| Variable | | non_IBS_1<br>non-IBS_1 |
| | Sample 1 | Sample 2 |
| Sample size | 76 | 115 |
| Lowest value | 0.1000 | 0.1000 |
| Highest value | 23.0000 | 19.0000 |
| Median | 5.0000 | 1.0000 |
| 95% Cl for the median | 4.0000 to 8.0000 | 1.0000 to 1.0000 |
| Interquartile range | 2.0000 to 9.0000 | 0.1000 to 3.0000 |

| Mann-Whitney test (independent samples) | |
|---|---|
| Average rank of first group | 127.1382 |
| Average rank of second group | 75.4217 |
| Mann-Whitney U | 2003.50 |
| Test statistic Z (corrected for ties) | 6.410 |
| Two-tailed probability | P < 0.0001 |

TABLE 12

| | | |
|---|---|---|
| Variable | | IBS_Test<br>IBS Test |
| Classification variable | | Diag<br>Diag |
| Sample size | | 191 |
| Positive group: | Diag = 1 | 76 |
| Negative group: | Diag = 0 | 115 |

TABLE 12-continued

| Disease prevalence (%) | unknown |
|---|---|

Area under the ROC curve (AUC)

| Area under the ROC curve (AUC) | 0.771 |
|---|---|
| Standard Error[a] | 0.0346 |
| 95% Confidence interval[b] | 0.705 to 0.828 |
| z statistic | 7.829 |
| Significance level P (Area = 0.5) | <0.0001 |

[a]DeLong et al., 1988
[b]Binomial exact

Youden index

| Youden index J | 0.4454 |
|---|---|
| 95% Confidence interval[a] | 0.2976 to 0.5542 |
| Associated criterion | >2 |
| 95% Confidence interval[a] | 0 to 2 |

[a]$BC_a$ bootstrap interval (1000 iterations).

Summary Table
Estimated specificity at fixed sensitivity

| Sensitivity | | 95% CI[a] | Criterion |
|---|---|---|---|
| | Specificity | | |
| 80.00 | 57.90 | 43.98 to 74.43 | >0.8364 |
| 90.00 | 41.68 | 30.23 to 52.71 | >0.1455 |
| 95.00 | 38.26 | 27.83 to 46.09 | >0 |
| 97.50 | 38.26 | 27.83 to 46.09 | >0 |
| | Sensitivity | | |
| 80.00 | 62.89 | 47.37 to 76.32 | >3.2 |
| 90.00 | 39.91 | 15.58 to 59.59 | >7.1667 |
| 95.00 | 15.62 | 5.83 to 32.66 | >11.0625 |
| 97.50 | 13.73 | 3.95 to 29.91 | >11.7812 |

[a]$BC_a$ bootstrap interval (1000 iterations).

Criterion values and coordinates of the ROC curve [Hide]

| Criterion | Sensitivity | 95% CI | Specificity | 95% CI | +LR | 95% CI | −LR | 95% CI |
|---|---|---|---|---|---|---|---|---|
| ≥0 | 100.00 | 95.3-100.0 | 0.00 | 0.0-3.2 | 1.00 | 1.0-1.0 | | |
| >0 | 92.11 | 83.6-97.0 | 38.26 | 29.4-47.8 | 1.49 | 1.3-1.7 | 0.21 | 0.09-0.5 |
| >1 | 77.63 | 66.6-86.4 | 61.74 | 52.2-70.6 | 2.03 | 1.6-2.6 | 0.36 | 0.2-0.6 |
| >2 | 72.37 | 60.9-82.0 | 72.17 | 63.0-80.1 | 2.60 | 1.9-3.6 | 0.38 | 0.3-0.6 |
| >3 | 64.47 | 52.7-75.1 | 79.13 | 70.6-86.1 | 3.09 | 2.1-4.6 | 0.45 | 0.3-0.6 |
| >4 | 56.58 | 44.7-67.9 | 83.48 | 75.4-89.7 | 3.42 | 2.2-5.4 | 0.52 | 0.4-0.7 |
| >5 | 48.68 | 37.0-60.4 | 87.83 | 80.4-93.2 | 4.00 | 2.3-6.9 | 0.58 | 0.5-0.7 |
| >6 | 43.42 | 32.1-55.3 | 88.70 | 81.4-93.8 | 3.84 | 2.2-6.8 | 0.64 | 0.5-0.8 |

Performance Metrics in Predicting IBS Status from Number of Positive Foods Using 90th Percentile of ELISA Signal to Determine Positive

TABLE 13

| Sex | No. of Positive Foods as Cutoff | Sensi-tivity | Spe-cificity | Positive Predictive Value | Negative Predictive Value | Overall Percent Agreement |
|---|---|---|---|---|---|---|
| F | 1 | 0.96 | 0.35 | 0.73 | 0.80 | 0.74 |
| | 2 | 0.82 | 0.53 | 0.76 | 0.64 | 0.72 |
| | 3 | 0.77 | 0.62 | 0.78 | 0.60 | 0.71 |
| | 4 | 0.68 | 0.67 | 0.79 | 0.54 | 0.68 |
| | 5 | 0.63 | 0.71 | 0.80 | 0.50 | 0.66 |
| | 6 | 0.57 | 0.76 | 0.81 | 0.50 | 0.64 |
| | 7 | 0.52 | 0.81 | 0.83 | 0.48 | 0.62 |
| | 8 | 0.46 | 0.85 | 0.84 | 0.46 | 0.60 |
| | 9 | 0.41 | 0.88 | 0.85 | 0.45 | 0.57 |
| | 10 | 0.34 | 0.88 | 0.85 | 0.43 | 0.54 |
| | 11 | 0.28 | 0.90 | 0.85 | 0.42 | 0.51 |

TABLE 13-continued

| Sex | No. of Positive Foods as Cutoff | Sensi-tivity | Spe-cificity | Positive Predictive Value | Negative Predictive Value | Overall Percent Agreement |
|---|---|---|---|---|---|---|
| | 12 | 0.21 | 0.94 | 0.85 | 0.40 | 0.48 |
| | 13 | 0.18 | 0.94 | 0.86 | 0.39 | 0.46 |
| | 14 | 0.15 | 0.95 | 0.89 | 0.39 | 0.45 |
| | 15 | 0.13 | 1.00 | 1.00 | 0.39 | 0.44 |
| | 16 | 0.11 | 1.00 | 1.00 | 0.38 | 0.43 |
| | 17 | 0.10 | 1.00 | 1.00 | 0.38 | 0.42 |
| | 18 | 0.07 | 1.00 | 1.00 | 0.38 | 0.41 |
| | 19 | 0.06 | 1.00 | 1.00 | 0.37 | 0.40 |
| | 20 | 0.04 | 1.00 | 1.00 | 0.37 | 0.39 |
| | 21 | 0.03 | 1.00 | 1.00 | 0.37 | 0.38 |
| | 22 | 0.03 | 1.00 | 1.00 | 0.36 | 0.37 |
| | 23 | 0.00 | 1.00 | 1.00 | 0.36 | 0.36 |
| | 24 | 0.00 | 1.00 | 1.00 | 0.36 | 0.36 |

Performance Metrics in Predicting IBS Status from Number of Positive Foods Using 90th Percentile of ELISA Signal to Determine Positive

TABLE 14

| Sex | No. of Positive Foods as Cutoff | Sensitivity | Specificity | Positive Predictive Value | Negative Predictive Value | Overall Percent Agreement |
|---|---|---|---|---|---|---|
| M | 1  | 0.81 | 0.35 | 0.29 | 0.85 | 0.46 |
|   | 2  | 0.71 | 0.57 | 0.35 | 0.86 | 0.61 |
|   | 3  | 0.67 | 0.68 | 0.41 | 0.86 | 0.68 |
|   | 4  | 0.62 | 0.75 | 0.45 | 0.86 | 0.72 |
|   | 5  | 0.53 | 0.80 | 0.48 | 0.84 | 0.74 |
|   | 6  | 0.47 | 0.85 | 0.50 | 0.83 | 0.76 |
|   | 7  | 0.39 | 0.88 | 0.50 | 0.82 | 0.76 |
|   | 8  | 0.30 | 0.90 | 0.50 | 0.80 | 0.75 |
|   | 9  | 0.25 | 0.92 | 0.50 | 0.79 | 0.75 |
|   | 10 | 0.18 | 0.93 | 0.43 | 0.78 | 0.74 |
|   | 11 | 0.14 | 0.94 | 0.43 | 0.77 | 0.74 |
|   | 12 | 0.11 | 0.95 | 0.40 | 0.77 | 0.75 |
|   | 13 | 0.10 | 0.96 | 0.43 | 0.76 | 0.75 |
|   | 14 | 0.07 | 0.97 | 0.50 | 0.76 | 0.75 |
|   | 15 | 0.06 | 0.97 | 0.50 | 0.76 | 0.75 |
|   | 16 | 0.06 | 0.98 | 0.50 | 0.76 | 0.75 |
|   | 17 | 0.05 | 0.98 | 0.33 | 0.76 | 0.75 |
|   | 18 | 0.00 | 0.98 | 0.00 | 0.75 | 0.75 |
|   | 19 | 0.00 | 0.98 | 0.00 | 0.75 | 0.75 |
|   | 20 | 0.00 | 1.00 | 0.00 | 0.75 | 0.75 |
|   | 21 | 0.00 | 1.00 | 0.00 | 0.75 | 0.75 |
|   | 22 | 0.00 | 1.00 | 0.00 | 0.75 | 0.75 |
|   | 23 | 0.00 | 1.00 | 0.00 | 0.75 | 0.75 |
|   | 24 | 0.00 | 1.00 |      | 0.75 | 0.75 |

What is claimed is:

1. A method of identifying one or more irritable bowel syndrome (IBS) trigger foods and reducing or relieving IBS symptoms for a patient known to have or is suspected of having IBS, the method comprising:
   contacting a bodily fluid of a patient that is known to have or is suspected of having IBS with a plurality of distinct IBS trigger food preparations immobilized on a solid carrier, wherein the distinct IBS trigger food preparations are food preparations having an IBS raw p-value of ≤0.07 or an IBS false discovery rate (FDR) multiplicity adjusted p-value of ≤0.10, and wherein the contacting is performed under conditions that allow antibodies from the bodily fluid to bind to at least one component of a distinct IBS trigger food preparation;
   detecting the antibodies bound to the at least one component of a distinct IBS trigger food preparation to obtain a first signal;
   assigning a predetermined percentile rank cutoff value for each of the distinct IBS trigger food preparations, wherein the predetermined percentile rank cutoff value is determined using an at least 90$^{th}$ percentile rank of a second signal from a control group;
   comparing the first signal to the predetermined percentile rank cutoff value;
   identifying one or more distinct IBS trigger foods positive for the patient known to have or suspected of having irritable bowel syndrome; and
   eliminating the one or more identified IBS trigger foods from the patient's diet.

2. The method of claim 1, further comprising updating or generating a report for the one or more distinct IBS trigger foods positive for the patient.

3. The method of claim 1, wherein the detecting comprises measuring or quantifying the antibodies via an immunoassay test.

4. The method of claim 3, wherein the bodily fluid is serum, and the solid carrier is a micro well plate.

5. The method of claim 1, wherein the bodily fluid is whole blood, plasma, serum, saliva or a fecal suspension.

6. The method of claim 1, wherein the plurality of distinct IBS trigger food preparations is coupled to the solid carrier in an individually addressable manner.

7. The method of claim 1, wherein the solid carrier is selected from the group consisting of an array, a micro well plate, a microfluidic device, a bead, an absorptive film, a dip stick, a chemical sensor, and an electrical sensor.

8. The method of claim 1, wherein at least two of the IBS trigger food preparations are selected from the group consisting of cocoa, tea, oat, cabbage, cow milk, onion, honey, rye, corn, yeast, wheat, soybean, egg, tuna, lemon, pineapple, cucumber, orange, halibut, walnut, grapefruit, cane sugar, chicken, blueberry, and shrimp.

9. The method of claim 1, wherein the solid carrier includes at least 10 distinct IBS trigger food preparations.

10. The method of claim 1, wherein the distinct IBS trigger food preparations are food preparations having an IBS raw p-value of ≤0.05 or an IBS FDR multiplicity adjusted p-value of ≤0.08.

11. The method of claim 10, wherein the solid carrier includes at least 8 distinct IBS trigger food preparations.

12. The method of claim 1, wherein at least ten of the distinct IBS trigger food preparations are selected from the group consisting of cocoa, tea, oat, cabbage, cow milk, onion, honey, rye, corn, yeast, wheat, soybean, egg, tuna, lemon, pineapple, cucumber, orange, halibut, walnut, grapefruit, cane sugar, chicken, blueberry, and shrimp.

13. The method of claim 1, wherein at least fifteen of the distinct IBS trigger food preparations are selected from the group consisting of cocoa, tea, oat, cabbage, cow milk, onion, honey, rye, corn, yeast, wheat, soybean, egg, tuna, lemon, pineapple, cucumber, orange, halibut, walnut, grapefruit, cane sugar, chicken, blueberry, and shrimp.

14. The method of claim 1, wherein the FDR multiplicity adjusted p-values are adjusted for at least one of age or gender.

15. The method of claim 1, wherein the plurality of distinct IBS trigger food preparations immobilized on a solid carrier are in a test panel, and the totality of food preparations in the test panel has an average IBS raw p-value of ≤0.05 or an average IBS false discover rate (FDR) multiplicity adjusted p-value of ≤0.08.

16. The method of claim 1, wherein the plurality of distinct IBS trigger food preparations immobilized on a solid carrier are in a test panel, and the totality of food preparations in the test panel has an average IBS raw p-value of ≤0.05 or an average IBS false discover rate (FDR) multiplicity adjusted p-value of ≤0.07.

17. A method of generating a test panel for food intolerance in a patient known to have or suspected of having irritable bowel syndrome (IBS), comprising:
   obtaining immunoassay results for a plurality of distinct food preparations, wherein the immunoassay results are based on bodily fluids of patients known to have or suspected of having IBS and bodily fluids of a control group not known to have or not suspected to have IBS;
   assigning a predetermined percentile rank cutoff value for each of the plurality of the distinct food preparations, wherein the predetermined percentile rank cutoff value is determined using an at least 90th percentile rank of the immunoassay results based on bodily fluids of the control group;

comparing the immunoassay results for the plurality of distinct food preparations based on bodily fluids of patients known to have or suspected of having IBS to the predetermined percentile rank cutoff value;

selecting a plurality of IBS trigger food preparations, wherein the IBS trigger food preparations are food preparations having an IBS raw p-value of ≤0.07 or an IBS false discovery rate (FDR) multiplicity adjusted p-value of ≤0.10;

immobilizing the plurality of IBS trigger food preparations to a solid carrier in an individually addressable manner, wherein the solid carrier is selected from the group consisting of an array, a micro well plate, a dipstick, a membrane-bound array, a microfluidic device, multiwell plate, a bead, an electrical sensor, a chemical sensor, a microchip and an adsorptive film, and generating a test panel comprising the selected IBS trigger food preparations.

18. The method of claim 17, wherein the selected IBS trigger food preparations include at least two food preparations selected from the group consisting of cocoa, tea, oat, cabbage, cow milk, onion, honey, rye, corn, yeast, wheat, soybean, egg, tuna, lemon, pineapple, cucumber, orange, halibut, walnut, grapefruit, cane sugar, chicken, blueberry, and shrimp.

19. The method of claim 17, further comprising stratifying the immunoassay results by gender for each of the distinct food preparations.

20. The method of claim 19, further comprising normalizing the immunoassay results to the patient's total IgG.

21. The method of claim 20, further comprising normalizing the immunoassay results to the global mean of the patient's food specific IgG results.

22. The method of claim 19, further comprising identifying a subset of patients, wherein the subset of patient sensitivities to the food preparations underlies IBS by raw p-value or an average discriminatory p-value of ≤0.01.

23. The method of claim 19, further comprising determining numbers of the food preparations, wherein the numbers of the food preparations can be used to confirm IBS by raw p-value or an average discriminatory p-value of ≤0.01.

24. A test panel generated according to claim 17, wherein the test panel includes nine or more IBS trigger food preparations, and wherein at least one of the selected IBS trigger food preparations is tuna or crab.

25. A test kit comprising the test panel according to claim 24.

* * * * *